(12) United States Patent
Ferguson et al.

(10) Patent No.: US 7,691,816 B2
(45) Date of Patent: Apr. 6, 2010

(54) PHARMACEUTICAL COMPOSITIONS

(75) Inventors: Mark Ferguson, Manchester (GB);
Sharon O'Kane, Manchester (GB);
Hugh Laverty, Manchester (GB); Nick Occleston, Manchester (GB); Jane Kelly, Manchester (GB); Wayne Burrill, Manchester (GB)

(73) Assignee: Renovo Ltd., Manchester (GB)

( * ) Notice: Subject to any disclaimer, the term of this patent is extended or adjusted under 35 U.S.C. 154(b) by 0 days.

(21) Appl. No.: 11/995,399

(22) PCT Filed: Jul. 12, 2006

(86) PCT No.: PCT/GB2006/002574

§ 371 (c)(1),
(2), (4) Date: Mar. 4, 2008

(87) PCT Pub. No.: WO2007/007095

PCT Pub. Date: Jan. 18, 2007

(65) Prior Publication Data

US 2008/0176799 A1 Jul. 24, 2008

(30) Foreign Application Priority Data

Jul. 12, 2005 (GB) .................... 0514259.1
Jul. 12, 2005 (GB) .................... 0514260.9

(51) Int. Cl.
*A61K 38/00* (2006.01)
*A01N 37/18* (2006.01)
*A01N 43/36* (2006.01)
*A61K 38/24* (2006.01)
*A23J 1/00* (2006.01)
*C07K 14/00* (2006.01)

(52) U.S. Cl. .................... 514/12; 514/2; 514/422; 530/399; 530/412; 530/350

(58) Field of Classification Search .................... None
See application file for complete search history.

(56) References Cited

U.S. PATENT DOCUMENTS

| 6,518,308 | B2 * | 2/2003 | Diamond .................... 514/557 |
| 7,341,994 | B2 * | 3/2008 | Ishikawa et al. ............... 514/12 |
| 2004/0151753 | A1 * | 8/2004 | Chen et al. .................... 424/426 |
| 2007/0072793 | A1 * | 3/2007 | Chung ........................... 514/9 |

FOREIGN PATENT DOCUMENTS

| WO | 93/10758 A1 | 6/1993 |
| WO | 98/04681 A1 | 2/1998 |
| WO | 01/48147 A1 | 7/2001 |

OTHER PUBLICATIONS

Martin 1997. Science 276:75-81.*
Meier et al. 2006. Expert Opin Emerging Drugs 11:39-47.*
Occleston et al. 2008. J Biomater. Sci. Polymer Edn. 19:1047-1063.*
Shah et al. 1995. J Cell Science 108:985-1002.*
Kaartinen et al 1995. Nature Genetics 11:415-421.*

* cited by examiner

*Primary Examiner*—Manjunath N Rao
*Assistant Examiner*—Shulamith H Shafer
(74) *Attorney, Agent, or Firm*—Darby & Darby P.C.

(57) ABSTRACT

The invention provides pharmaceutical compositions comprising TGF-β superfamily members and sugars, the compositions allowing improved recovery and/or increased biological activity of the TGF-β superfamily member incorporated therein. The invention also relates to uses of sugars to improve the recovery or increase the biological activity of TGF-β superfamily members in a pharmaceutical composition. Uses of the pharmaceutical compositions are also described, particularly with reference to wound healing and fibrosis. Furthermore, the invention discloses medicaments for the prevention or reduction of injection pain.

31 Claims, 3 Drawing Sheets

2A

IC$_{50}$ = 34.793pg/mL

2F

IC$_{50}$ = 8.758pg/mL

2B

IC$_{50}$ = 24.136pg/mL

2G

IC$_{50}$ = 5.957pg/mL

2C

IC$_{50}$ = 22.055pg/mL

2H

IC$_{50}$ = 7.72pg/mL

IC$_{50}$ = 30.562pg/mL

IC$_{50}$ = 7.31pg/mL

IC$_{50}$ = 38.973pg/mL

IC$_{50}$ = 6.798pg/mL

SEQUENCE LISTING

<160> NUMBER OF SEQ ID NOS: 3

<210> SEQ ID NO 1
<211> LENGTH: 112
<212> TYPE: PRT
<213> ORGANISM: Homo sapiens

<400> SEQUENCE: 1

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 2
<211> LENGTH: 112
<212> TYPE: PRT
<213> ORGANISM: Homo sapiens

<400> SEQUENCE: 2

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 3
<211> LENGTH: 112
<212> TYPE: PRT
<213> ORGANISM: Homo sapiens

<400> SEQUENCE: 3

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

-continued

| Pro | Tyr | Leu | Arg | Ser | Ala | Asp | Thr | Thr | His | Ser | Thr | Val | Leu | Gly | Leu |
|  | 50 |  |  |  |  | 55 |  |  |  | 60 |  |  |  |  |  |
| Tyr | Asn | Thr | Leu | Asn | Pro | Glu | Ala | Ser | Ala | Ser | Pro | Cys | Cys | Val | Pro |
| 65 |  |  |  |  | 70 |  |  |  | 75 |  |  |  |  |  | 80 |
| Gln | Asp | Leu | Glu | Pro | Leu | Thr | Ile | Leu | Tyr | Tyr | Val | Gly | Arg | Thr | Pro |
|  |  |  |  | 85 |  |  |  |  | 90 |  |  |  |  | 95 |  |
| Lys | Val | Glu | Gln | Leu | Ser | Asn | Met | Val | Val | Lys | Ser | Cys | Lys | Cys | Ser |
|  |  |  | 100 |  |  |  |  | 105 |  |  |  |  | 110 |  |  |

PHARMACEUTICAL COMPOSITIONS

CROSS-REFERENCE TO PRIOR APPLICATIONS

This is a U.S. National Phase Application under 35 U.S.C. §371 of International Patent Application No. PCT/GB2006/002574 filed Jul. 12, 2006, which claims the benefit of GB Patent Application Nos. 0514259.1 filed Jul. 12, 2005 and 0514260.9 filed Jul. 12, 2005, all of which are incorporated by reference herein. The International Application was published in English on Jan. 18, 2007 as WO 2007/007095 A2 under PCT Article 21(2).

BACKGROUND OF THE INVENTION

The present invention relates to pharmaceutical compositions comprising TGF-β superfamily members. Particularly, the invention provides improved pharmaceutical compositions comprising TGF-β superfamily members, wherein the compositions provide improved recovery of the TGF-β superfamily members and/or improved biological activity of the TGF-β superfamily members incorporated in the compositions. The invention also provides methods utilising such pharmaceutical compositions. Furthermore, the invention also provides medicaments for the prevention or reduction of injection pain.

The Transforming Growth Factor-Betas (TGF-βs) represent a family of cytokines having diverse biological activities. The TGF-βs belong to a wider group of related cytokines known as the TGF-β superfamily. Members of the TGF-β superfamily include activins, bone morphogenetic proteins (BMPs), anti-Müllerian hormone (AMH), the glial cell line derived neurotrophic factor (GDNF) subfamily and the growth/differentiation factor (GDF) subfamily. TGF-β superfamily members share structural similarities, such as a common cysteine knot motif, as well as common signal transduction pathways. Illustrative examples of members of the TGF-superfamily are shown in FIG. 1.

The biological activities of members of the TGF-β superfamily have utility in many different therapeutic contexts, and accordingly there is much interest in the pharmaceutical application of TGF-β superfamily members.

TGF-$β_1$, TGF-$β_2$ and TGF-$β_3$ are known to play crucial roles in the regulation of the wound healing response, while osteoinduction modulated by BMPs is useful in the therapeutic application of bone formation, healing and remodelling.

TGF-β1 has uses in the prevention and/or treatment of scleroderma, angiogenesis disorders, renal disease, osteoporosis, bone disease, glomerulonephritis and renal disease.

TGF-β2 may be used in the treatment of glioma, non-small-cell lung cancer, pancreas tumour, solid tumours, colon tumour, ovary tumour, age-related macular degeneration, ocular injury, osteoporosis, retinopathy, ulcers, carcinoma, mouth inflammation and scleroderma.

TGF-β3 may be used in the treatment of fibrotic disorders, scleroderma, angiogenesis disorders, restenosis, adhesions, endometriosis, ischemic disease, bone and cartilage induction in vitro fertilisation, oral mucositis, renal disease, prevention, reduction or inhibition of scarring, enhancement of neuronal reconnection in the peripheral and central nervous system, preventing, reducing or inhibiting complications of eye surgery (such as LASIK or PRK surgery).

Many other members of the TGF-β superfamily are also known to have therapeutic applications. For example, glial cell line derived neurotrophic factor (GDNF) has been suggested to be useful in the treatment of many neurodegenerative and neurological diseases (such as Parkinson's disease, motor neurone disease, Alzheimer's disease, and Huntington's chorea) as well as in wound healing, treatment of scar tissue and ocular applications in treatment of corneal tissue and corneal disease.

Artemin (which is also known as neublastin or enovin) is suitable for use in the prevention and/or treatment of neurodegenerative disease, neuropathic pain and neuropathy.

Neurturin has therapeutic applications in Parkinson's disease and other neurological diseases.

Persephin is believed to have therapeutic utility in the treatment of such conditions as inflammation, multiple sclerosis, neoplasm, healing of wounds and other injuries, Acquired immune deficiency syndrome (AIDS), bacterial, viral and other infections, immune deficiency, Alzheimer's disease, Huntington's chorea, Parkinson's disease, cerebrovascular ischemia, and degenerative diseases.

BMP 15 (also known as Growth Differentiation Factor 9B) is useful in the treatment of female infertility, in contraception, as well as in cases of bone injury and wound healing.

The superfamily member GDF9 has therapeutic utility in the treatment of female infertility.

Nodal may be used in the treatment of muscle disease, osteoporosis, osteoarthritis, wound healing, periodontal disease and connective tissue disease.

BMP3 has medical uses in the fields of bone injury, osteoporosis, wound healing, nervous system injury, neurodegenerative disease, Parkinson's disease, cerebrovascular disease and renal disease. BMP3b may be used in the treatment of birth complications.

BMP-5 may be used to treat many of the same indications as BMP-3, as well as osteoporosis, connective tissue disease, injury including wound healing, bone disease, tooth disease, osteoarthritis, periodontal disease, cerebrovascular ischemia, renal failure and brain injury.

GDF-5 (also known as cartilage derived morphogenetic factor) may be used in the treatment of arthritis, arthropathy, and neoplasm.

BMP10 may be used to treat osteoporosis, wound healing, ulcer, periodontal disease, bone disease, burns, connective tissue disease, bone tumour, bone injury and neoplasm.

BMP-8 (also known as osteogenic protein 2) may be used in the treatment of bone disease.

BMP-6 has therapeutic applications in the treatment of cerebrovascular ischemia and cancer.

BMP-7 may be used in the treatment of renal disease, calcification, tooth disease, motor neurone disease, Parkinson's disease, periodontal disease, bone diseases, cerebrovascular ischemia, renal failure, brain injury, scar tissue, musculoskeletal disease, and osteoporosis.

BMP-2 may be used for treating osteoporosis, bone diseases including musculoskeletal diseases and periodontal disease.

BMP-4 may be used in the treatment of kidney diseases.

GDF-3 has therapeutic uses in the treatment of immune disorders, whereas GDF-1 may be used in the treatment of nervous system injuries, multiple sclerosis and neurological diseases.

GDF-8 (also known as myostatin) may be used in the prevention and/or treatment of muscle wasting disease and non-insulin dependent diabetes.

The inhibin family of proteins may be used to treat infertility, haematological disease, anaemia, carcinoma, leukaemia and hyperphosphatemia and cancers, as well as in contraception.

Activin has therapeutic uses in the fields of scleroderma, angiogenesis disorders, scarring and fibrosis, restenosis, adhesions, endometriosis, ischemic disease, bone and cartilage induction, in vitro fertilisation, oral mucositis and wound healing.

GDF-15 may be used to treat Parkinson's disease, Alzheimer's disease, schizophrenia, cerebrovascular ischemia, dementia, immune disorders and neoplasm.

Mullerian inhibitory factor (MIF), which is also known as anti-Mullerian hormone or MIS, may be used in the fields of cancer including metastasis, lymphoid leukaemia, prostate tumour, uterine cervix tumour, breast tumour, ocular tumour, ovary tumour endocrine disease, haemangioma, endometriosis, inflammation, melanoma, neoplasm, carcinoma, skin tumour, female genital tract tumour, male genital system disease, erectile dysfunction and respiratory distress syndrome.

Ebaf (also known as Lefty) may be used in the treatment of hair disease including alopecia, scleroderma, fibrosis, muscular dystrophy, neoplasm, autoimmune disease, treatment of scar tissue, cirrhosis, pulmonary fibrosis, melanoma and carcinoma.

Despite the well-recognised requirement for pharmaceutical compositions comprising TGF-β superfamily members there are many acknowledged problems associated with presently existing compositions. Among these problems are the common inability to recover a proportion of a TGF-β superfamily member incorporated in a given composition (a problem which may arise as a result of adsorption of the TGF-β superfamily member to the material of a container in which the composition is stored), and a generally observed decrease over time of the biological activity of TGF-β superfamily members incorporated and stored in compositions. This also has important implications in the manufacture of any TGF-β superfamily member therapeutic.

BRIEF SUMMARY OF THE INVENTION

It is an object of the present invention to obviate or mitigate at least some of the problems associated with prior art pharmaceutical compositions comprising TGF-β superfamily members.

According to the present invention there is provided a pharmaceutical composition comprising a TGF-β superfamily member and a sugar provided at sufficient concentration to allow improved recovery and/or increased biological activity of the TGF-β superfamily member.

The present invention also provides use of a sugar for improving the recovery and/or increasing the biological activity of a TGF-β superfamily member incorporated in a pharmaceutical composition. It will be appreciated that the increase in biological activity may be assessed after recovery of the TGF-β from the composition. Preferably the amount of a TGF-β superfamily member recovered from the pharmaceutical composition may be increased, and this recovered TGF-β superfamily member may have increased biological activity. Suitable sugars and TGF-β superfamily members (and concentrations of both sugars and superfamily members) for use in accordance with this aspect of the invention may be selected based on any of the considerations set out elsewhere in this specification with reference to any of the aspects or embodiments of the invention. In particular TGF-β may be a suitable superfamily member, and maltose may be a preferred sugar. The combination of maltose and TGF-β$_3$ may be particularly preferred.

Preferably a TGF-β superfamily member incorporated in a pharmaceutical composition in accordance with the invention will exhibit increased biological activity (i.e. the biological activity exhibited by a TGF-β superfamily member incorporated in a pharmaceutical composition of the invention will be greater than for the same quantity of the same superfamily member incorporated in a prior are composition).

Most preferably a pharmaceutical composition of the invention should allow improved recovery of a TGF-β superfamily member that has been incorporated, and the superfamily member will additional exhibit increased biological activity.

BRIEF DESCRIPTION OF THE DRAWINGS

The invention will be further described, by way of example, with reference to the accompanying Experimental Results and Figures, in which:

FIG. 2A shows a first standard curve generated using prior art formulation DS11, in which TGF-β3 has an IC$_{50}$ of 34.793 pg/mL. FIG. 2B shows a second standard curve generated using prior art formulation DS11, in which TGF-β3 has an IC$_{50}$ of 24.136 pg/mL. FIG. 2C shows a third standard curve generated using prior art formulation DS11, in which TGF-β3 has an IC$_{50}$ of 22.055 pg/mL. FIG. 2D shows a fourth standard curve generated using prior art formulation DS11, in which TGF-β3 has an IC$_{50}$ of 30.562 pg/mL. FIG. 2E shows a fifth standard curve generated using prior art formulation DS11, in which TGF-β3 has an IC$_{50}$ of 39.973 pg/mL. FIG. 2F shows a first standard curve generated using a maltose formulation in accordance with the invention, in which TGF-β3 has an IC$_{50}$ of 8.758 pg/mL. FIG. 2G shows a second standard curve generated using a maltose formulation in accordance with the invention, in which TGF-β3 has an IC$_{50}$ of 5.957 pg/mL. FIG. 2H shows a third standard curve generated using a maltose formulation in accordance with the invention, in which TGF-β3 has an IC$_{50}$ of 7.72 pg/mL. FIG. 2I shows a fourth standard curve generated using a maltose formulation in accordance with the invention, in which TGF-β3 has an IC$_{50}$ of 7.31 pg/mL. FIG. 2J shows a fifth standard curve generated using a maltose formulation in accordance with the invention, in which TGF-β3 has an IC$_{50}$ of 6.798 pg/mL.

Figure 1:
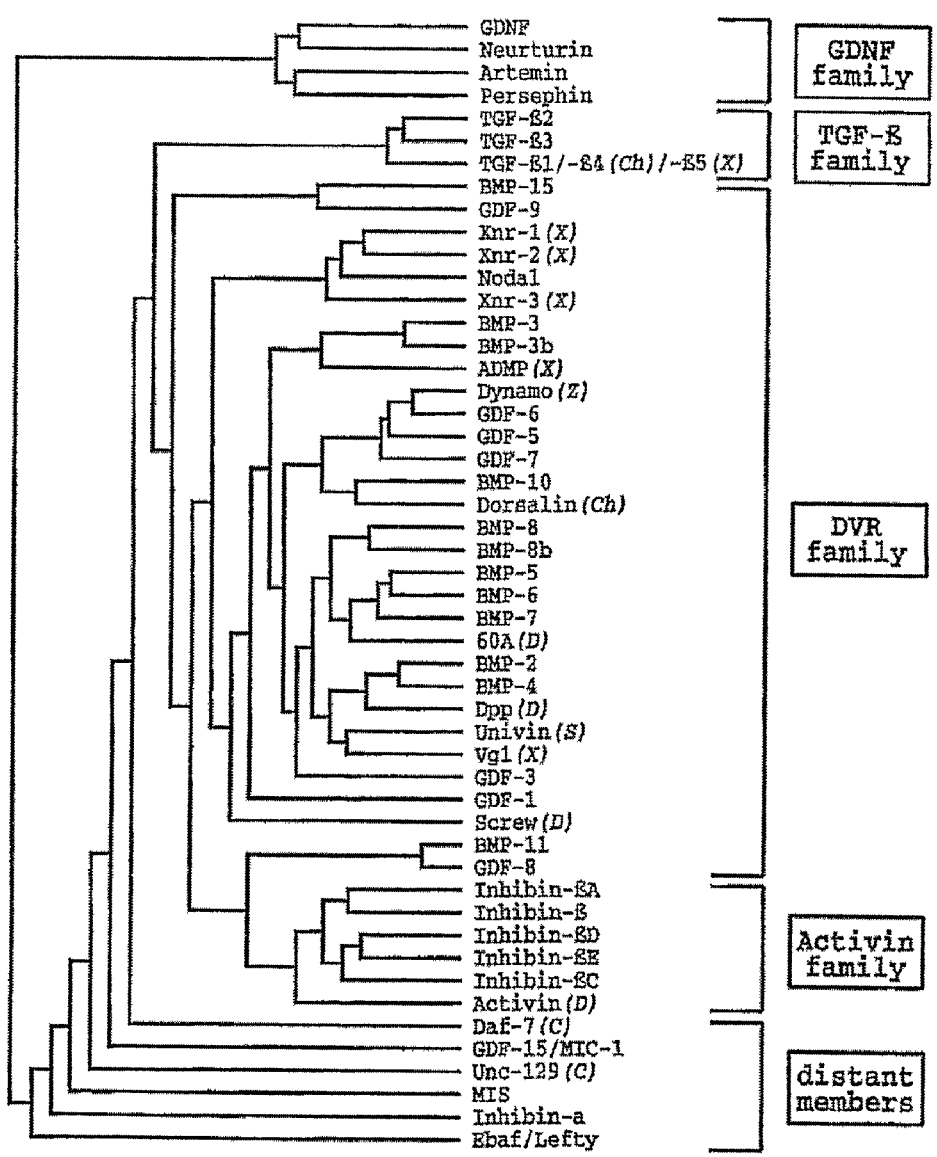
FIG. 1 illustrates members of the TGF-β superfamily, and the relationships between superfamily members.

Table 1 compares the quantity of a TGF-β superfamily member recoverable from pharmaceutical compositions of the invention with the quantity recoverable from known compositions of the prior art;

Table 2 compares the biological activity of TGF-β superfamily members recovered from pharmaceutical compositions in accordance with the invention with the biological activity of TGF-β superfamily members recovered from known prior art compositions;

Table 3 shows the results of an assessment of injection pain comparing the results achieved using medicaments manufactured in accordance with the invention with results obtained using prior art compositions; and Table 4 summarises the results shown in Table 4.

DETAILED DESCRIPTION OF THE INVENTION

The inventors have found that the beneficial effects conferred by pharmaceutical compositions in accordance with the invention can be obtained using any sugar thus far tested. However, it may be preferred that pharmaceutical compositions in accordance with the invention comprise a sugar selected from the group comprising maltose, sucrose glucose and mannose. More preferably the sugar utilised in pharmaceutical compositions in accordance with the invention may be selected from the group comprising maltose and sucrose, and most preferably the sugar is maltose.

For the avoidance of doubt, terms as "pharmaceutical compositions of the invention" (or the like) are intended to encompass not only compositions as defined in the first, third and fourth aspects of the invention, but also pharmaceutical compositions manufactured in accordance with the uses of the invention.

The present invention is based on the inventors' finding that pharmaceutical compositions comprising TGF-β superfamily members in the presence of suitable sugars, or suitable concentrations of sugars, provide a number of surprising advantages when compared to pharmaceutical compositions known in the prior art. These advantages include a two- to five-fold increase in the recovery of TGF-β superfamily members from pharmaceutical compositions of the invention, as well as a four-fold increase in the biological activity of TGF-β superfamily members incorporated in such compositions.

In a preferred embodiment of the invention there is provided a pharmaceutical composition comprising a TGF-β superfamily member and a sugar, the sugar being present at a concentration of greater than 50 mg/ml, for use as a medicament. A composition in accordance with the invention may comprise a sugar provided at a concentration of between 51 and 200 mg/ml, preferably at a concentration of between 60 and 150 mg/ml, more preferably at a concentration of between 70 and 100 mg/ml, even more preferably at a concentration of between 80 and 95 mg/ml, and most preferably at a concentration of between 85 and 90 mg/ml.

In a further preferred embodiment of the invention there is provided a pharmaceutical composition comprising a TGF-β superfamily member and a sugar selected from the group comprising glucose and mannose, for use as a medicament.

Previously, the prior art has suggested that the sugar alcohol mannitol represents a preferred excipient for use in pharmaceutical compositions comprising TGF-β superfamily members. The inventors have found that pharmaceutical compositions in accordance with the present invention provide advantages and beneficial effects even when compared to these preferred prior art compositions. Indeed, the surprisingly efficacious compositions of the invention allow two- to five-fold increased recovery of an incorporated TGF-β superfamily member compared to such mannitol-based formulations, as well as up to a four-fold increase in biological activity.

Compositions in accordance with the invention provide benefits over the prior art both in terms of the improved recovery of TGF-β superfamily members and the increased inherent biological activity of TGF-β superfamily members incorporated in such compositions. The prior art contains no indication that sugars may be used to such great effect, and certainly contains no suggestion that the use of compositions comprising sugars at a concentration of greater than 50 mg/ml provide any of the advantages identified by the inventors.

The increased recovery of TGF-β superfamily members incorporated in compositions in accordance with the invention confers many important advantages over known compositions previously disclosed in the prior art. There is nothing in the prior art to suggest that sugars selected from the group comprising glucose and mannose may provide these advantages identified by the present inventors.

The skilled person will appreciate that, there are certain contexts in which, suitable pharmaceutically acceptable derivatives, variants and salts of sugars may also be used in the pharmaceutical compositions of the invention. Suitable derivatives, variants or salts may be those of a sugar selected from the group comprising maltose, sucrose glucose and mannose, and in particular those based on sugars selected from the group comprising maltose and sucrose (more preferably on the sugar maltose). However, the inventors believe that the benefits identified are most readily conferred by use of the sugars themselves. This is in contrast to, and should be distinguished from, the prior art's suggested use of agents such as sugar alcohols. In keeping with these advantages it will be appreciated that sugar alcohols should not be used in accordance with the present invention.

The inventors have found that the pharmaceutical compositions in accordance with the invention are suitable for use with any TGF-β superfamily member. Accordingly, except for where the context requires otherwise, references to TGF-β or TGF-βs may be taken to encompass reference to any member of the TGF-β superfamily. It will be appreciated that such references should be taken to encompass all known superfamily members, and at least all members of the TGF-β superfamily set out in FIG. 1. Preferably the TGF-β superfamily member incorporated in pharmaceutical compositions in accordance with the present invention may be selected from the group comprising TGF-$\beta_1$, TGF-$\beta_2$ and TGF-$\beta_3$ (corresponding to Sequence IDs No.s 1, 2 and 3 respectively). Most preferably the TGF-β superfamily member is TGF-$\beta_3$.

The skilled person will further appreciate that the pharmaceutical compositions of the invention may incorporate more than one TGF-β superfamily member. Such compositions incorporating multiple TGF-β superfamily members may be preferred in contexts where it is wished to take advantage of combinations of TGF-β superfamily members having an additive or synergistic interaction in their combined therapeutic or biological effects. Accordingly, except for where the context requires otherwise, references to a TGF-β superfamily member, and particularly a TGF-β superfamily member incorporated in a pharmaceutical composition of the invention, should be taken also to encompass compositions incorporating two or more TGF-β superfamily members.

It is well known to those skilled in the art that proteins such as TGF-β superfamily members have a tendency to interact, particularly with hydrophobic components of a composition or storage vessel, such that they are not available to exert their biological or therapeutic activities on administration of a composition in which they are incorporated. This problem is exacerbated on storage of compositions containing TGF-β superfamily members. Storage of such compositions increases the inaccessibility of the TGF-β superfamily member so incorporated. It is believed that the incidence of binding of the TGF-β superfamily member molecules within the composition, as well as to components of a vessel in which the composition is stored, increases over time of storage. The binding of the TGF-β superfamily member molecules, either within the composition itself or to other substrates (such as storage vessels), results in a lack of availability of the bound molecules to achieve their biological and/or therapeutic activity. After prolonged storage the reduction in available biological and/or therapeutic activity of the incorporated TGF-β superfamily member may become so pronounced that the composition is rendered biologically and/or therapeutically ineffective.

In comparison with known pharmaceutical compositions, such as those using mannitol as an excipient, pharmaceutical compositions in accordance with the present invention allow recovery of a significantly higher proportion of the total amount of the TGF-β superfamily member originally incorporated in a pharmaceutical composition. For the present purposes "recovery" of a TGF-β superfamily member from a composition may be taken to refer to the proportion of the TGF-β superfamily member incorporated in the composition that is available to exert a therapeutic and/or biological activity on administration of the composition. A model by which recovery of a TGF-β superfamily member from a pharmaceutical composition of interest (either a prior art composition or a composition of the invention) may be investigated is described in the Experimental Results section below. It will be appreciated that, although the major benefit of increased recovery lies in the increased biological activity that may be exerted, when assessing recovery the method used need not measure biological activity. Suitable methods may, instead, be based on chemical or physical indications as to the amount of a TGF-β superfamily member recovered (e.g. the weight recoverable).

As noted above, the inventors have found that pharmaceutical compositions in accordance with the present invention allow a two- to five-fold increase in recovery of incorporated TGF-β superfamily members when compared to mannitol-based compositions. Such results may be obtained using compositions utilising sugars at a concentration of greater than 50 mg/ml. Typically pharmaceutical compositions using sucrose or mannose allow a two- to three-or-more-fold increase in recoverable TGF-β superfamily members as compared to the prior art. The increased recovery achieved using mannose as compared to mannitol highlights to benefits of using sugars as opposed to sugar alcohols.

As a result of their capacity to allow improved recovery of TGF-β superfamily members incorporated in the compositions, pharmaceutical compositions in accordance with the present invention confer marked advantages as compared to prior art compositions. It will be appreciated that, in order to be able to recover a therapeutically effective amount of a TGF-β superfamily member on administration of a prior art composition, it is necessary to incorporate in the composition a greater quantity of the TGF-β superfamily member than the therapeutically effective amount that it is wished to recover (since a certain proportion of the total amount of the TGF-β superfamily member incorporated in the prior art composition will be rendered unrecoverable, for example through binding within the composition or to the storage vessel). Accordingly the prior art composition must be manufactured such that it incorporates a total amount equivalent to the sum of:

i) the therapeutically effective amount of the TGF-β superfamily member; and
ii) the amount of the TGF-β superfamily member that will be rendered unrecoverable.

Since the pharmaceutical compositions of the invention allow greater recovery of incorporated TGF-β superfamily members the total amount of the TGF-β superfamily member that must be incorporated in such compositions at manufacture (in order to enable recovery of the desired therapeutically effective amount of the TGF-β superfamily member) may be relatively reduced. It will be appreciated that the ability to achieve a desired therapeutic effect by use of a pharmaceutical composition incorporating a relatively smaller amount of a TGF-β superfamily member provides considerable commercial advantages over the prior art.

Despite progress allowing increased efficiency and cost-effectiveness in the manufacture of therapeutically useful proteins such as TGF-β superfamily members, these biologically and therapeutically active proteins remain relatively expensive to produce and are typically the most expensive components of pharmaceutical compositions in which they are incorporated. In contrast, sugars represent relatively inexpensive compounds to be used in pharmaceutical compositions. It will be appreciated that compositions of the invention, in which the amount of a TGF-β superfamily member recoverable from the composition is increased by means of the incorporation in the composition of relatively cheap sugars, provide considerable economic benefits over compositions known in the prior art.

The increased recovery of TGF-β superfamily members incorporated in pharmaceutical compositions in accordance with the invention also means that such compositions have increased "shelf life" as compared to known compositions. It will be appreciated that the ability to recover a higher proportion of a TGF-β superfamily member from a composition of the invention that has been stored means that compositions in accordance with the present invention may be used for a longer period after their manufacture than is the case with prior art compositions. For example, the tendency of TGF-β superfamily members incorporated in prior art compositions to become unrecoverable from the compositions after a prolonged period of storage is dramatically reduced when using compositions of the present invention. This increased shelf life is further improved by the notable increase in the inherent biological activity of TGF-β superfamily members incorporated in compositions of the invention discussed below.

In addition to improved recovery of TGF-β superfamily members from pharmaceutical compositions in accordance with the present invention, the inventors have surprisingly found that pharmaceutical compositions in accordance with the invention are also able to beneficially increase the inherent biological activity of TGF-β superfamily members incorporated therein.

The inherent biological activity of a TGF-β superfamily member incorporated in a pharmaceutical compositions of the invention may, for example, be measured with reference to the ability of the TGF-β superfamily member to inhibit the proliferation of mink lung epithelial cells (MLECs). A model by which the inherent biological activity of a TGF-β superfamily member incorporated in a composition of interest may be determined is presented in the Experimental Results section below.

Alternatively, the inherent biological activity to be assessed may be an activity that is specific to the TGF-β superfamily member in question. For example, in the case of pharmaceutical compositions of the invention incorporating the preferred TGF-β superfamily member TGF-$\beta_3$, the inherent biological activity may be the ability to reduce and/or inhibit scarring or fibrosis.

The inventors have discovered that TGF-β superfamily members incorporated in pharmaceutical compositions in accordance with the present invention exhibit up to five times the biological activity demonstrated by TGF-β superfamily members incorporated in prior art compositions. This marked increase in biological activity of TGF-β superfamily members incorporated in pharmaceutical compositions of the invention represents a surprising and important advantage of these compositions. Indeed, there is nothing in the prior art that suggests that pharmaceutical compositions in accordance with the present invention should be able to increase the biological activity of TGF-β superfamily members incorporated therein.

It will be readily appreciated that the improved biological activity exhibited by TGF-β superfamily members incorporated in pharmaceutical compositions in accordance with the invention will be particularly advantageous in contexts in which it is desired to utilise the biological activity of TGF-β superfamily members therapeutically. Since almost all therapeutic applications of the members of the TGF-β superfamily rely upon the biological activity of the superfamily member, the increased biological activity of TGF-β superfamily members incorporated in compositions according to the invention corresponds directly with an increase in therapeutic activity.

There are many therapeutic contexts in which it is known to employ pharmaceutical compositions incorporating TGF-β superfamily members. Examples of such contexts include the treatment of wound healing; the prevention and/or treatment of scarring; the prevention and/or treatment of fibrosis; the acceleration of wound healing; the promotion of epithelial regeneration; the inhibition of scarring and/or fibrosis; and therapeutic applications of osteoinduction (e.g. osteoinduction in bone building; healing; and/or remodelling) and in the other therapeutic contexts described in the introduction.

The inventors have found that pharmaceutical compositions in accordance with the present invention are particularly suitable for use in the context of wound healing and/or fibrosis. Pharmaceutical compositions in accordance with the invention are suitable for use in the promotion of wound healing with reduced scarring; the prevention and/or treatment of fibrosis; the inhibition of scarring and/or fibrosis; the acceleration of wound healing; and the promotion of epithelial regeneration. Accordingly it will be recognised that pharmaceutical compositions in accordance with the present invention may be used in the preparation of medicaments for:

i) the promotion of wound healing with reduced scarring; and/or
ii) the prevention and/or treatment of fibrosis; and/or
iii) the inhibition of scarring and/or fibrosis; and/or
iv) the acceleration of wound healing; and/or
v) the promotion of epithelial regeneration.

It will be appreciated that the benefits in terms of improved recovery of TGF-β superfamily members from compositions of the invention and the increased biological activity of TGF-β superfamily members incorporated in such compositions may be (to at least some extent) separated from one another according to the manner in which the pharmaceutical compositions are formulated. In other words, compositions in accordance with the present invention may be produced in which:

i) the composition provides the benefits of both improved recovery of the TGF-β superfamily member incorporated therein, and increased biological activity of the TGF-β superfamily member; or
ii) the composition provides the benefits of improved recovery of the TGF-β superfamily member incorporated therein, but not of increased biological activity; or
iii) the composition does not provide improved recovery of the TGF-β superfamily member, but does provide increased biological activity thereof.

Examples illustrating these various options are provided below.

For example, compositions in accordance with the first aspect of the invention may preferably comprise a TGF-β superfamily member and a sugar at an effective concentration (e.g. greater than 50 mg/ml) both during storage of the composition, for the present purposes taken to encompass the time occurring between the manufacture of the composition and its eventual use, and also at the time at which the composition is administered. Such compositions in accordance with this aspect of the invention benefit from the advantages of improved recovery of the TGF-β superfamily member during and after storage, and also from increased biological activity of the TGF-β superfamily member when administered.

It will be appreciated that compositions in accordance with the present invention also encompass those compositions in which the sugar is present at an effective concentration (e.g. greater than 50 mg/ml) during storage, but wherein the sugar is present at a lower concentration at the time of administration. A typical example of such a situation is one in which the composition is diluted prior to its administration. Although compositions in accordance with this embodiment of the invention do not comprise a sugar at an effective concentration (e.g. greater than 50 mg/ml) at the time of administration of the composition the compositions still benefit from the increased recovery of the TGF-β superfamily member after storage, and also from increased biological activity of the TGF-β superfamily member at the time of its recovery.

In a further embodiment of compositions in accordance with the present invention, the effective concentration (e.g. greater than 50 mg/ml) of the sugar may only be established relatively shortly before the composition is administered. A typical example of a composition according to this embodiment may be one in which a solvent is added to an otherwise "dry" composition prior to administration to produce a composition in which the sugar has the requisite effective concentration (e.g. greater than 50 mg/ml). Compositions in accordance with this embodiment of the invention provide TGF-β superfamily members having surprisingly high biological activity (compared with prior art compositions) to the site at which they are administered. The problems associated with recovery of TGF-β superfamily members after storage associated with prior art compositions may be obviated by the storage of the composition in a relatively inert dry state.

Indeed, so advantageous is this embodiment of the invention that, in accordance with a third aspect of the invention, there is provided a soluble pharmaceutical composition comprising TGF-β superfamily member and a sugar, wherein the sugar is provided in such a proportion that, on dissolution of the composition to achieve a physiological solution, the sugar is provided at sufficient concentration to allow improved recovery and/or increased biological activity of the TGF-β superfamily member. Preferably the sugar is provided in such a proportion that on dissolution of the composition to achieve a physiological solution the concentration of the sugar is greater than 50 mg/ml. The sugar may preferably be maltose.

Preferably a pharmaceutical composition in accordance with this third aspect of the invention may be a water-soluble pharmaceutical composition. A physiological solution in accordance with this aspect of the invention may be a solution having physiological concentration or osmolarity. For example, a soluble pharmaceutical composition in accordance with this aspect of the invention suitable for injection in mammals may, on dissolution of the composition, achieve an osmolarity of approximately 290 milliosmolar (osmole per liter). It will be appreciated that compositions in accordance with this third aspect of the invention confer all the advantages relating to increased biological activity of the TGF-β superfamily member incorporated therein that are found in compositions in accordance with the first and second aspects of the invention. Accordingly, compositions in accordance with this third aspect of the invention are suitable for all medical and/or therapeutic uses described above in relation to compositions in accordance with the first and second aspects of the invention.

One of the factors determining whether or not a composition is considered suitable for safe injection into mammals such as humans is the concentration of sodium ions present in the composition at the time of administration. Accordingly, in a fourth aspect of the invention, there is provided a soluble pharmaceutical composition comprising a TGF-β superfamily member, a source of sodium ions, and a sugar, the quantities of the source of sodium ions and of the sugar being such that on dissolution of the composition to produce a sodium concentration of between 130 and 160 mEq/L, the concentration of the sugar is sufficient to allow improved recovery and/or increased biological activity of the TGF-β superfamily member. Preferably, the quantities of the source of sodium ions and of the sugar are such that on dissolution of the composition to produce a sodium concentration of between 130 and 160 mEq/L the concentration of the sugar is greater than 50 mg/ml. The sugar may preferably be maltose. Sources of sodium ions suitable for use in injectable pharmaceutical compositions will be well known to those of skill in the art. Preferably compositions in accordance with this fourth aspect of the invention may be water-soluble compositions. It will further be appreciated that these compositions of the fourth aspect of the invention may also be employed in accordance with the medical and/or therapeutic uses described above.

In addition to the use of pharmaceutical compositions in accordance with the invention in therapeutic applications, the skilled person will also appreciate that the increased biological activity exhibited by compositions according to the invention may also be of benefit in contexts in which the biological activity of TGF-β superfamily members is to be utilised for non-therapeutic purposes. Typically, such non-therapeutic uses of TGF-β superfamily members may relate to their use for research or experimental purposes. Accordingly, the invention also provides compositions as recited in the first, second or third aspects of the invention for use other than as a medicament, and particularly for research and/or experimental use.

The inventors have found that although the advantages conferred by pharmaceutical compositions in accordance with the present invention are made available through all formulations tested the pharmaceutical compositions of the invention are particularly advantageous when the compositions are formulated for administration by injection. More preferably, pharmaceutical compositions in accordance with the invention may be formulated for intradermal injection, or may be formulated for subcutaneous injection. Typical formulations suitable for intradermal injection and/or subcutaneous injection will be well known to those skilled in the art.

Pharmaceutical compositions in accordance with the invention suitable for localised parenteral administration (e.g. intradermal, intramuscular and subcutaneous) and systemic parenteral administration (e.g. intravenous and intra-arterial) may be prepared by mixing a TGF-β superfamily member and sugar (both having the desired degree of purity) with optional physiologically acceptable carriers, excipients or stabilizers in the form of; lyophilised and non-lyophilised powder formulations for reconstitution prior to use, non-aqueous and aqueous solutions, and semi-solid formulations. Acceptable carriers, including excipients, are non-toxic to recipients at the dosages and concentrations employed, and include, but are not limited to, buffers such as phosphates, citrates, and other organic acids; antioxidants including ascorbic acid and methionine; tonicity modifiers such as sodium chloride, glycerol, and the like; preservatives such as octadecyldimethylbenzyl ammonium chloride; hexamethonium chloride; benazalkonium chloride, benzethonium chloride; phenol, butyl or benzyl alcohol; alkyl parabens such as methyl and/or propyl and/or butyl paraben; catechol; resorcinol; cyclohexanol; 3-pentanol; and m-cresol); low molecular weight polypeptides (comprising less than about ten amino acid residues); proteins, such as serum albumin, gelatin, or immunoglobulins; hydrophilic polymers such as polyvinylpyrrolidone; amino acids such as glycine, glutamine, asparagine, histidine, arginine, or lysine; carbohydrates including dextrins; chelating agents such as EDTA; salt-forming counter-ions such as sodium; metal complexes (e.g., Zn-protein complexes); anionic surfactants such as fatty acid soaps, acyl sulfates, or acyl sulfosuccinates; cationic surfactants, such as alkyl primary, secondary, tertiary, or quaternary amines; non-ionic surfactants, for example, sorbitan esters or polyethoxylated esters of acyl acids, copolymers of polyethylene oxide and polypropylene oxide.

By way of example, a pharmaceutical composition of the invention in the form of a sterile solution suitable for parenteral administration, may include the following constituents in addition to the TGF-β superfamily member and sugar:

0.01 M to 0.1 M phosphate buffer, and

Sodium chloride up to 0.9% w/v (to achieve iso-tonicity with blood, 290-300 mOsm/L), and 0.1 mg/ml polyoxyethylene sorbitan mono-oleate (Tween™ 80).

A lyophilized (freeze-dried) powder 'cake' of the above solution could be prepared.

Such a pharmaceutical composition in accordance with the invention could be presented in the form of a vial, an ampoule, or a pre-filled syringe of, either; a sterile solution, a sterile suspension or any other pharmaceutically acceptable form of presentation suited to localised parenteral drug delivery.

The improved recovery and increased biological activity of TGF-β superfamily members incorporated in pharmaceutical compositions in accordance with the invention generally means that they may be used as an alternative to existing approaches, such as lyophilisation, used to improve the shelf-lives of compositions containing TGF-β superfamily members. Accordingly, it may generally be preferred that a pharmaceutical composition of the invention is non-lyophilised. However, it may be wished that known techniques, such as lyophilisation, be used in accordance with the compositions of the invention. These techniques may still further extend the shelf life of pharmaceutical compositions of the invention, and may be used to produce, for example, a sterile lyophilised (freeze-dried) powder suitable for reconstitution.

Pharmaceutical compositions in accordance with the invention may be formulated for use in the eye (for instance as eye drops), or as intraperitoneal instillates.

Alternatively, or additionally, pharmaceutical compositions in accordance with the invention may be formulated for topical administration. The topical administration of pharmaceutical compositions in accordance with the invention may be particularly preferred in the context of follow up care for a site at which the TGF-β superfamily member is exerting a therapeutic effect.

Pharmaceutical compositions of the invention suitable for topical administration (e.g. transdermal/cutaneous, ocular, otic, nasal, pharyngeal, buccal, rectal, vaginal, urethral) may be prepared by mixing a TGF-β superfamily member and a sugar (both having the desired degree of purity) with optional physiologically acceptable carriers, excipients or stabilisers in the form of lyophilised or non-lyophilised powder formulations, non-aqueous or aqueous solutions, non-aqueous or aqueous dispersions/suspensions, including emulsions and semi-solid formulations. Acceptable carriers, including excipients, are non-toxic to recipients at the dosages and concentrations employed, and include, but are not limited to, purified water, saline, phosphate-buffered saline (PBS) Ringer's solution, Ringer's-lactate solution, hydro-alcoholic solutions, polyethylene glycol (PEG), propylene glycol (PG), phosphates, acetates, gelatin, collagens, Carbopol 934™ (BF Goodrich Corp.), vegetable and synthetic oils and waxes, anionic surfactants such as fatty acid soaps, acyl sulfates, or acyl sulfosuccinates; cationic surfactants, such as alkyl primary, secondary, tertiary, or quaternary amines; non-ionic surfactants, for example, sorbitan esters or polyethoxylated esters of acyl acids, copolymers of polyethylene oxide and polypropylene oxide, and the like. Pharmaceutical compositions of the invention may additionally include suitable preservatives, stabilisers, antioxidants, anti-microbials and buffering agents, for example, methyl and/or propyl and/or butyl parabens, butylated hydroxy anisole (BHA), butylated hydroxy toluene (BHT), citric acid, ascorbic acid, and the like. Emulsion, cream or ointment bases useful in formulation may include aqueous-based creams and emulsions (oil-in-water), oil-based creams and emulsions (water-in-oil), ointments (emulsifying and non-emulsifying hydrocarbon), gels, hydrogels, and the like. Other formulations for topical delivery may include aerosols, bandages, and other wound dressings. Alternatively pharmaceutical composition of the invention one may incorporate or encapsulate in a suitable polymer matrix or membrane, thus providing a sustained-release delivery device suitable for placement on, or implantation near, a site to be treated.

A pharmaceutical composition of the present invention in the form of a semi-solid hydrogel formulation suitable for topical administration may further comprise the following constituents (in addition to the TGF-β superfamily member and sugar):

0.1% w/v to 2.0% w/v hydroxy cellulose, and
0.1% w/v to 1.0% w/v Carbopol 934™ (BF Goodrich Corp.), and
10 to 20% w/v propylene glycol, and
0.005% w/v to 0.020% w/v methyl paraben, and
0.005% w/v to 0.020% w/v propyl paraben, and
Sodium hydroxide or hydrochloric acid q.s. ad pH 4-10
Purified water, q.s. ad 100% w/v Suitable pharmaceutical compositions of the invention may be presented in the form of a bottle, a jar, a tube, a spray, of, either; a sterile solution; a sterile lyophilized or non-lyophilized powder for reconstitution, a sterile dispersion/suspension, a sterile semi-solid, or any other pharmaceutically acceptable form of presentation suited to topical drug delivery.

Pharmaceutical compositions of the invention suitable for oral administration may be prepared by mixing the TGF-β superfamily member and sugar (both having the desired degree of purity) with optional physiologically acceptable carriers, excipients or stabilisers in the form of powder or granule formulations, non-aqueous or aqueous solutions, non-aqueous or aqueous dispersion/suspension formulations including emulsions, semi-solid formulations, tablet (uncoated or coated) or capsule (hard or soft) formulations having either immediate release and/or modified release (enteric/delayed/sustained) characteristics. Acceptable carriers, including excipients, are non-toxic to recipients at the dosages and concentrations employed, and include, but are not limited to, purified water, saline, phosphate-buffered saline (PBS) Ringer's solution, Ringer's-lactate solution, hydroalcoholic solutions, cellulose and cellulose derivatives, starch and modified starches, polyethylene glycol (PEG), propylene glycol (PG), phosphates, acetates, gelatin, collagens, Carbopol 934™ (BF Goodrich Corp.), vegetable and synthetic oils and waxes, anionic surfactants such as fatty acid soaps, acyl sulfates, or acyl sulfosuccinates; cationic surfactants, such as alkyl primary, secondary, tertiary, or quaternary amines; non-ionic surfactants, for example, sorbitan esters or polyethoxylated esters of acyl acids, copolymers of polyethylene oxide and polypropylene oxide, and the like.

The TGF-β superfamily member may be dispersed within a liquid formulation either as a suspension within the liquid (for example as a colloidal suspension), or dissolved within the liquid as a solution. For present purposes, a solution may be considered to be characterised as comprising a liquid solvent throughout which is dispersed a homogeneous distribution of a TGF-β superfamily member that will not subsequently settle out of the solution.

Pharmaceutical compositions in accordance with the present invention may preferably comprise aqueous solutions. Suitable pharmaceutical compositions may be liquid compositions, or alternatively may further comprise thickening agents such that a gel or semi-solid composition is formed. Suitable thickening agents are well known to those skilled in the art, and include methylcellulose. The use of thickening agents in pharmaceutical compositions in accordance with the first, second, or third aspects of the invention may be advantageous in a number of contexts. Particularly, the use of thickening agents in compositions of the invention may be advantageous in ensuring that the composition is retained in the site at which it is administered and at which it is desired for the composition to have its biological and/or therapeutic effect. This advantage is of benefit in relation to topical medicaments, and may be applicable to both medicaments for external application (such as thickened creams or gels) and medicaments for internal application (for example thickened gels for local injection). It will be appreciated that thixotropic formulations of pharmaceutical compositions in accordance with the invention may be beneficial in a number of applications, for example in the use of nasal sprays or inhalers used to administer compositions to the lungs (which may otherwise be relatively inaccessible) for the prevention and/or treatment of lung fibrosis or scarring.

The pharmaceutical compositions of the invention may preferably be provided in pre-filled vessels containing the composition. Such pre-filled vessels provide advantages in terms of their ability to readily deliver compositions, and particularly pre-sterilised compositions, to the location at which the composition is to be employed. Suitable vessels may be selected with reference to the chosen formulation and the method or route by which the composition is to be administered, and will typically include vessels such as vials or syringes. The provision of pharmaceutical compositions comprising TGF-β superfamily members in such pre-filled vessels has previously been compromised by the tendency for the TGF-β superfamily member protein to adhere to the walls of the vessel over time. Furthermore, the tendency of TGF-β superfamily members stored in vessels to degenerate and lose activity over time has also limited the suitability of compositions comprising TGF-β superfamily members to be pre-filled and stored in this way. Thus the pharmaceutical compositions of the present invention provide a solution to failings of the prior art that have previously prevented or discouraged the provision of otherwise desirable pre-filled vessels, and particularly vessels containing sterile compositions.

As previously indicated, the pharmaceutical compositions of the invention are well suited for therapeutic use. Accordingly, in a fifth aspect of the invention there is provided a method of treatment comprising administering to an individual in need of the therapeutic activity of a TGF-β superfamily member a therapeutic amount of a composition in accordance with the first, second, third or fourth aspects of the invention. The therapeutic activity should be understood to encompass prophylactic therapy, including the prevention of diseases or conditions that may be treated using the therapeutic activity of the TGF-β superfamily member.

A preferred use of pharmaceutical compositions according to the invention is in the context of wound healing and/or scar prevention/reduction. The inventors have found that pharmaceutical compositions of the invention may be used in the preventions and/or inhibition of scarring. Alternatively or additionally the pharmaceutical compositions of the invention may be used in the preventions and/or treatment of fibrosis. The pharmaceutical compositions of the invention may also be used to promote wound healing. In promoting wound healing and/or prevention or inhibition of scar formation it may be preferred or necessary to administer the pharmaceutical composition before or after the formation of a wound. Accordingly, the pharmaceutical composition will be present in the wounded area, either through its introduction into the wound, or through the formation of the wound at a site where the pharmaceutical composition is already present (by virtue of earlier administration). It will therefore be appreciated that pharmaceutical compositions in accordance with the invention may preferably be formulated such that they are well tolerated by the wounded site. Formulations for application to wounds may preferably make use of a pharmaceutical vehicle that is relatively "mild". Suitable vehicles may be biocompatible, biodegradable and bioresorbable and bioresolvable. Preferred formulations may exclude substances that stimulate inflammation, and may preferably include anti-inflammatory agents.

A suitable method by which prevention and/or inhibition of scarring may be assessed is described in the inventors' co-pending application published as WO2006/064207.

So beneficial is the use of pharmaceutical compositions in accordance with the invention in the healing of wounds and inhibition of scarring that, in a sixth aspect of the invention, there is provided a method of promoting wound healing and/or inhibiting scar formation, the method comprising administering to a patient in need of such promotion and/or inhibition a therapeutically effective amount of a pharmaceutical composition in accordance with the first, second, third or fourth aspects of the invention. In the context of the present invention, promotion of healing may be considered to encompass an increase in the rate of healing and/or an increase in the quality of healing. The inhibition of scar formation may be considered to encompass any degree of inhibition (which may range from partial inhibition to total inhibition) of scarring associated with wound healing or other fibrotic processes characterised by the abnormal or excessive deposition of fibrous tissue. The pharmaceutical compositions and methods of treatment of the invention may be particularly useful in the prevention, reduction, inhibition or treatment of scarring (fibrosis) associated with fibrotic disorders selected from the group consisting of: skin fibrosis; scleroderma; progressive systemic fibrosis; lung fibrosis; muscle fibrosis; kidney fibrosis; glomerulosclerosis; glomerulonephritis; uterine fibrosis; renal fibrosis; cirrhosis of the liver, liver fibrosis; chronic obstructive pulmonary disease; fibrosis following myocardial infarction; central nervous system fibrosis, such as fibrosis following stroke; fibrosis associated with neuro-degenerative disorders such as Alzheimer's Disease or multiple sclerosis; fibrosis associated with proliferative vitreoretinopathy (PVR); restenosis; endometriosis; ischemic disease and radiation fibrosis. The medicaments and methods of treatment of the invention may also be useful in the prevention, reduction or management of fibrosis associated with rheumatoid arthritis.

Prevention and/or treatment in accordance with the present invention may be particularly useful in the case of wounds at risk of an aberrant wound healing or scarring response. For example, prevention and/or treatment in accordance with the sixth aspect of the invention may be particularly preferred in the treatment of chronic wounds (such as ulcers) or of wounds predisposed to development into chronic wounds (for example wounds of diabetics, the elderly or patients with polypharmacy). Prevention and/or treatment in accordance with the sixth aspect of the invention may also be of particular benefit in the treatment of pathological scars (such as keloid or hypertrophic scars) or of wounds predisposed to the development of pathological scars (such as burns wounds, the wounds of children, the wounds of Afro-Caribbean or Mongoloid individuals, or wounds at positions of heightened skin tension).

Pharmaceutical compositions in accordance with the present invention are particularly suited to administration to the skin, for example in the treatment of dermal wounds. However, the compositions may be used effectively in the treatment of other wound types including, but not limited to, wounds of the eye; wounds of the digestive system; wounds of the nervous system; wounds of the urino-genital system; wounds of the respiratory system; wounds of the kidneys; tendon and ligament wounds; and wounds of the heart or circulatory system, adhesions formed after injury and restenosis. The inventors believe that pharmaceutical compositions and methods of treatment of the invention are suitable for use in the skin; use in the eye (including the prevention, reduction or inhibition of scarring resulting from eye surgery such as LASIK or PRK surgery); use in blood vessels; use in the peripheral or central nervous system (where prevention, reduction or inhibition of scarring may enhance neuronal reconnection); use in tendons, ligaments or muscle; use in the oral cavity, including the lips and palate (such as in preventing, reducing or inhibiting scarring resulting from treatment of cleft lip or palate); use in the internal organs such as the liver, heart, brain, digestive tissues and reproductive tissues; and use in body cavities such as the abdominal cavity, pelvic cavity and thoracic cavity (where prevention, reduction or inhibition of scarring may reduce the number of incidences of adhesion formation and/or the size of adhesions formed). The medicaments and methods of the invention may be used to prevent, reduce or inhibit adhesions, such as those occurring in the abdomen, pelvis or spine. It is particularly preferred that the medicaments and methods of the invention be used to prevent, reduce or inhibit scarring of the skin (dermal scarring).

Pharmaceutical compositions of the present invention may preferably be administered prior to wounding and/or the onset of scarring (which for the present purpose should be taken to include fibrosis associated with fibrotic disorders). The pharmaceutical composition may be administered up to 24 hours before wounding, preferably up to ten hours before wounding, more preferably up to five hours before wounding, and most preferably up to an hour before wounding. It will be appreciated that the administration of pharmaceutical compositions in accordance with the invention prior to wounding or the onset of scarring is of particular utility in the case of elective wounds (such as those associated with surgical procedures) or situations in which there is a recognised risk of the initiation of scarring (i.e. predisposition to fibrosis or exposure to stimuli likely to induce fibrosis).

As an alternative, the pharmaceutical composition may be administered after wounding or the onset of scarring. In the case of administration of the pharmaceutical composition after wounding, it may be preferred that the pharmaceutical composition be administered immediately after wounding, or at least as soon as practicable after wounding (for example after admission of a wounded patient into the care of a physician). In the case of administration of the pharmaceutical composition after the onset of scarring, such as scarring arising as a result of a fibrotic disorder, the composition may preferably be administered immediately after the initiation of scarring is recognised. In either case the pharmaceutical composition may preferably be administered up to a week after wounding or the onset of scarring, more preferably up to 24 hours after wounding or onset of scarring, yet more preferably up to five hours, even more preferably up to five hours, and most preferably up to an hour after wounding or the onset of scarring.

The pharmaceutical compositions in accordance with the invention may be formulated for topical application. Suitable formulations in accordance with this embodiment of the invention may include liquid, cream, ointment or gel formulations, or spray or aerosol formulations.

The methods or medicaments of the invention may be used prophylactically, at sites where no wound exists but where a wound that would otherwise give rise to a scar or chronic wound is to be formed. By way of example medicaments in accordance with the invention may be administered to sites that are to undergo wounding as a result of elective procedures (such as surgery), or to sites that are believed to be at elevated risk of wounding. It may be preferred that the medicaments of the invention are administered to the site immediately prior to the forming of a wound (for example in the period up to six hours before wounding) or the medicaments may be administered at an earlier time before wounding (for example up to 48 hours before a wound is formed). The skilled person will appreciate that the most preferred times of administration prior to formation of a wound will be determined with reference to a number of factors, including the formulation and route of administration of the selected medicament, the dosage of the medicament to be administered, the size and nature of the wound to be formed, and the biological status of the patient (which may determined with reference to factors such as the patient's age, health, and predisposition to healing complications or adverse scarring). The prophylactic use of methods and medicaments in accordance with the invention is a preferred embodiment of the invention, and is particularly preferred in the promotion of accelerated wound healing with reduced scarring in the context of surgical wounds.

The methods and medicaments of the invention are also able to promote accelerated wound healing with reduced scarring if administered after a wound has been formed. It is preferred that such administration should occur as early as possible after formation of the wound, but agents of the invention are able to promote accelerated wound healing with reduced scarring at any time up until the healing process has been completed (i.e. even in the event that a wound has already partially healed the methods and medicaments of the invention may be used to promote accelerated wound healing with reduced scarring in respect of the remaining un-healed portion). It will be appreciated that the "window" in which the methods and medicaments of the invention may be used to promote accelerated wound healing with reduced scarring is dependent on the nature of the wound in question (including the degree of damage that has occurred, and the size of the wounded area). Thus in the case of a large wound the methods and medicaments of the invention may be administered relatively late in the healing response yet still be able to promote accelerated wound healing with reduced scarring. The methods and medicaments of the invention may, for instance, preferably be administered within the first 24 hours after a wound is formed, but may still promote accelerated wound healing with reduced scarring if administered up to ten, or more, days after wounding.

The methods and medicaments of the invention may be administered on one or more occasions as necessary in order to promote accelerated wound healing with reduced scarring. For instance therapeutically effective amounts of the medicaments may be administered to a wound as often as required until the healing process has been completed. By way of example, the medicaments of the invention may be administered daily or twice daily to a wound for at least the first three days following the formation of the wound.

Most preferably the methods or medicaments of the invention may be administered both before and after formation of a wound. The inventors have found that administration of the medicaments of the invention immediately prior to the formation of a wound, followed by daily administration of such agents in the days following wounding, is particularly effective in promoting accelerated wound healing with reduced scarring.

It will be appreciated that the amount of a pharmaceutical composition in accordance with the invention that should be applied to a wound depends on a number of factors such as the biological activity and bioavailability of the TGF-β superfamily member incorporated in the medicament. This in turn may depend on factors such as the identity of the TGF-β superfamily member and the mode of administration of the composition. Other factors in determining a suitable therapeutic amount of a composition in accordance with the invention may include:

i) The half-life of the TGF-β superfamily member in the subject being treated.
ii) The specific condition to be treated (e.g. acute wounding, chronic wounds or fibrotic disorders).
iii) The age of the subject being treated.

The frequency of administration of compositions in accordance with the invention will be influenced by the above-mentioned factors and particularly by the half-life of the TGF-β superfamily member incorporated in the composition within the subject being treated.

Generally when pharmaceutical compositions in accordance with the invention are to be used in the treatment of existing wounds the composition should be administered as soon as the wound has occurred (or in the case of wounds that are not immediately apparent, such as those at internal body sites, as soon as the wound has been diagnosed). Therapy with compositions or methods in accordance with the invention should continue until the healing process has been promoted (and/or scarring inhibited) to a clinician's satisfaction.

As noted above, frequency of administration of compositions in accordance with the invention will depend upon the biological half-life of the TGF-β superfamily member incorporated therein. Typically a composition in accordance with the invention formulated as a cream or ointment should be administered to a target tissue such that the concentration of the TGF-β superfamily member in the target tissue is maintained at a level suitable for having a therapeutic effect. This may require administration daily or even several times daily.

Pharmaceutical compositions in accordance with the invention, may be administered by any suitable route capable of achieving a desired biological or therapeutic effect (such as the promotion of wound healing or inhibition of scarring), but it is preferred that the compositions be administered locally at the site at which the activity is required e.g. by injection.

The inventors find that the promotion of accelerated wound healing and/or the inhibition of scarring using pharmaceutical compositions in accordance with the present invention is particularly improved by topical application of the composition to a wound (or, in the case of prophylactic application, to a tissue or site where a wound is to be formed).

Pharmaceutical compositions in accordance with the invention may take a number of different forms depending, in particular on the manner in which they are to be used. Thus, for example, they may be in the form of a liquid, ointment, cream, gel, hydrogel or aerosol. All of such compositions are suitable for topical application to a wound, which is a preferred means of administering agents of the invention to a subject (person or animal) in need of treatment.

Pharmaceutical compositions in accordance with the invention may be provided on a sterile dressing or patch, which may be used to cover a site at which it is desired that the TGF-β superfamily member incorporated in the composition should have a biological or therapeutic effect. It will be appreciated that the advantages provided by pharmaceutical compositions in accordance with the invention, in terms of improved shelf-life, increased recovery and/or increased biological activity of the incorporated TGF-β superfamily member, mean that such compositions are particularly suitable for incorporation in pre-prepared patches or dressing.

Pharmaceutical compositions in accordance with the invention are particularly suitable for incorporation within slow or delayed release devices, since the compositions are able to obviate many of the disadvantages normally associated with the storage of compositions incorporating TGF-β superfamily members. Suitable devices may, for example, be placed on or inserted under the skin and the composition incorporating the TGF-β superfamily member released over days, weeks or even months. Such a device may be particularly useful for patients that require long-term administration of the TGF-β superfamily member. Examples of conditions that may particularly benefit from such long-term administration of pharmaceutical compositions in accordance with the invention include the treatment of chronic wounds or of extensive acute wounds (such as burns) and the treatment of established fibrotic conditions.

Daily doses of pharmaceutical compositions in accordance with the invention may be given as a single administration (e.g. a daily injection or a daily application of a topical formulation). Alternatively, pharmaceutical compositions in accordance with the invention may require administration twice or more times during a day. In a further alternative, a slow release device may be used to provide a patient with a suitable dose of a pharmaceutical composition in accordance with the invention without the need to administer repeated doses.

Liquid vehicles may be used in preparing solutions, suspensions, emulsions, syrups, elixirs and pressurized compositions. The agent of the invention can be dissolved or suspended in a pharmaceutically acceptable liquid vehicle such as water, an organic solvent, a mixture of both or pharmaceutically acceptable oils or fats. It is preferred that liquid pharmaceutical compositions in accordance with the invention are provided as aqueous solutions.

The liquid vehicle can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration.

The liquid vehicle for pressurized compositions can be halogenated hydrocarbon or other pharmaceutically acceptable propellant.

Liquid pharmaceutical compositions of the invention formulated as sterile solutions or suspensions can be administered by intramuscular, intrathecal, epidural, intraperitoneal, intradermal or subcutaneous injection. Sterile solutions can also be administered intravenously. It will be appreciated that injectable compositions in accordance with the invention may also include binders, suspending agents and preservatives as necessary. Suitable examples of such agents will be well known to those skilled in the art.

The inventors have also found that pharmaceutical compositions in accordance with the invention are suitable for oral administration. Suitable formulations for use in accordance with this embodiment of the invention include mouth washes and the like. Orally administered pharmaceutical compositions in accordance with the invention may be used in the prevention and/or treatment of mucositis, ulcers (including gastrointestinal and stomach ulcers) Chrohn's Disease and ulcerative colitis.

Pharmaceutical compositions in accordance with the invention are suitable for administration to the eye. Accordingly a preferred formulation of compositions of the invention for such use may be in the form of eye drops. It is known that TGF-β superfamily members such as TGF-$β_3$ may be used in the promotion of accelerated wound healing with reduced scarring in the cornea. Corneal wounds may result from trauma to the eye arising as a result of accidental injury (as considered above) or as a result of surgical operations (e.g. laser surgery on the cornea).

Pharmaceutical compositions of the invention may be used in a range of "internal" sites (i.e. sites occurring within the body, rather than on an external surface). Thus for example, medicaments in accordance with the invention may be formulated for inhalation for use in the nose, lungs or other respiratory epithelia. Examples where it may be desirable to use the pharmaceutical compositions of the invention in this manner include the treatment of internal wounds, and the prevention and/or treatment of scarring or fibrosis in the respiratory system.

The use at internal body sites of pharmaceutical compositions in accordance with the present invention may also be advantageous in the treatment of wounds at elevated risk of forming adhesions. Such adhesions are a common result of injuries or wounds in the digestive or urino-genital systems, and can lead to deleterious loss of function in afflicted tissues.

Known procedures, such as those conventionally employed by the pharmaceutical industry (e.g. in vivo experimentation, clinical trials etc.), may be used to establish specific or preferred formulations of pharmaceutical compositions in accordance with the invention, as well as precise therapeutic regimes for administration of such compositions (such as daily doses of the TGF-β superfamily member incorporated in the composition and the frequency and route of administration of the composition).

A suitable daily dose of a pharmaceutical composition in accordance with the invention for use in wound healing depends upon a range of factors including (but not limited to) the desired therapeutic activity to be achieved by the composition (for instance acceleration of healing and/or the prevention or inhibition of scarring); the identity of the TGF-β superfamily member incorporated in the composition; the nature of the tissue wounded; the area and/or depth of the wound to be treated; the severity of the wound; and the presence or absence of factors predisposing to pathological scar or chronic wound formation. Typically a suitable dose of a TGF-β (such as TGF-β$_3$) superfamily member to be administered by means of a pharmaceutical composition in accordance with the invention will be within the range of 0.001 ng to 100 mg of the superfamily member per 24 hours, although this figure may be modified upwards or downwards in response to the factors outlined above. The amount of the TGF-β superfamily member administered by means of the pharmaceutical composition of the invention may preferably be 50 to 500 ng per linear centimeter of tissue damage.

Generally, pharmaceutical compositions in accordance with the invention should be formulated such that when administered to a wound a concentration of the incorporated TGF-β superfamily member (e.g. TGF-β3) of between 10 ng/100 μl and 500 ng/100 μl per linear centimeter is achieved. Preferably the TGF-β superfamily member may be provided at concentrations of between 50 ng/100 μl and 250 ng/100 μl per linear centimeter.

The skilled person will appreciate that the concentration of a TGF-β superfamily member that it may be desired to bring about in a tissue to be treated by administration of a pharmaceutical composition in accordance with the invention will be dependent upon the potency of the family member, and on the particular cell and tissue types that it is desired to treat.

In the case of a typically superfamily member (such as TGF-β3) of 110-170 amino acids length it may be preferred that pharmaceutical compositions of the invention be administered to achieve a local concentration of approximately 19 nM to 100 nM, and more preferably between 19.664 nM and 98.321 nM, in the tissue to be treated.

Pharmaceutical compositions in accordance with the invention may be used therapeutically as a monotherapy, which is to say the desired therapeutic activity being brought about solely through the use of pharmaceutical compositions in accordance with the invention. Alternatively the methods or pharmaceutical compositions of the invention may be used in combination with other compounds or treatments to achieve the desired therapeutic effect. Suitable treatments that may be used as parts of such combination therapies will depend on the therapeutic effect that it is desired to achieve, but will be well known to those skilled in the art.

A highly surprising advantage of pharmaceutical compositions of the invention (and methods of treatment using such compositions) is that the inventors have found that the administration of these compositions by injection is associated with greatly reduced injection pain and erythema compared to that observed on administration of prior art compositions. This benefit is highly advantageous since the pharmaceutical compositions of the invention are highly suitable for administration by injection.

However, the inventors believe that the advantage of reduced injection pain may also be achieved using pharmaceutical compositions that do not comprise TGF-β3 superfamily members.

Accordingly, in a seventh aspect of the present invention there is provided the use of a sugar in the manufacture of a medicament for the prevention or reduction of injection pain.

This seventh aspect of the invention is based on the inventors' surprising finding that pharmaceutical compositions comprising sugars give rise to reduced pain when administered to a subject. Particularly, the inventors have found that injectable pharmaceutical compositions comprising sugars give rise to reduced injection pain when injected into a subject, and in a preferred embodiment of the invention there is provided the use of a sugar in the preparation of an injectable medicament for the prevention or reduction of injection pain.

In an eighth aspect of the invention there is provided a method of preventing or reducing injection pain comprising administering to a patient in need of such pain prevention or reduction an effective amount of a medicament comprising a sugar. It is preferred that medicaments administered in accordance with this aspect of the invention be injectable medicaments.

Medicaments in accordance with, or suitable for use in, these aspects of the invention, may be manufactured and formulated in accordance with techniques and formulations described with reference to preceding aspects of the invention.

Injection pain is a generally recognised medical problem, and is one of the most important adverse effects militating against the use of injectable pharmaceuticals or compositions, and injection pain (or the fear of injection pain) may cause considerable anxiety in patients requiring injections. For the present purposes injection pain may be taken to refer to pain associated with the introduction of hypodermic needles, catheters, cannulae, and other such devices into the body of a subject.

It is frequently necessary to administer injections to patients at sites that are already subject to sensations of pain and this may exacerbate the level of pain perceived by the recipient of the injection. Examples of such situations include injections at wound sites, injections associated with the treatment of infections, and injections associated with treatment of autoimmune diseases. In many of these cases existing inflammation at the site where the injection is to take place may increase a patient's perception of pain associated with the injection.

Even in the absence of inflammation or other factors predisposing to heightened injection pain the natural aversion of patients to the pain of injections has a number of deleterious effects. It is recognised that injection pain is one of the major underlying reasons why patients may not initiate or complete therapeutic regimes in which medicaments are administered by injection. In the case of babies and young children the adverse reaction of the subject can also be traumatic for the parent or guardian responsible for the subject receiving the injection.

These problems associated with injection pain may be partially (or even totally) alleviated by medicaments manufactured in accordance with the seventh aspect of the invention, or methods of treatment in accordance with the eighth aspect of the invention.

The inventors believe that the advantages provided by medicaments manufactured in accordance with the seventh aspect of the present invention are also provided by all medicaments of the invention (i.e. medicaments in accordance with the other aspects of the invention). Thus, except for where the context requires otherwise, the advantages described below in connection with the medicaments of the seventh aspect of the invention (and the methods of the eighth aspect of the invention) should be considered to be provided by all pharmaceutical compositions of the invention (since all comprise the sugars believed to be responsible for the prevention or reduction of injection pain).

One of the notable advantages of the medicaments of the invention is their very rapid action in preventing or reducing injection pain. Medicaments of the invention are able to exert their activity against injection pain almost instantaneously on their injection into a patient. Accordingly, medicaments manufactured in accordance with the invention are able to effectively prevent or reduce injection pain that would otherwise arise as a result of the injection through which the medicaments are administered to a patient.

It will be recognised that the immediate action of medicaments manufactured in accordance with the invention provides many advantages in a clinical context. By using medicaments manufactured in accordance with the invention it is not necessary to pre-treat a patient or injection site in order to alleviate or prevent injection pain. This is of considerable importance since many medical practitioners act under considerable time pressure, and the additional time expenditure associated with existing pre-treatment regimes aimed to reduce injection pain is one of the major factors that adversely influences the employment of such regimes in practice. Indeed, even the perception that the use of existing pre-treatment regimes requires considerable expenditure of time prevents their wider application. Since the medicaments of the invention can be administered by means of the very injection the pain of which it is desired to reduce it will be appreciated that their use adds no additional time to the process of administering the injection.

The skilled person will immediately appreciate that medicaments manufactured in accordance with the methods of the invention (and particularly those manufactured in accordance with the seventh aspect of the invention) may be used as "carriers" incorporating other active agents. By incorporating these further active agents in medicaments manufactured in accordance with the invention it is possible to administer the active agents to a patient by means of injection with the advantage that the patient to whom the medicament is being administered experiences reduced injection pain. Accordingly, it is a preferred embodiment of the invention that medicaments manufactured in accordance with the invention further comprise an active agent to be administered with reduced injection pain.

An "active agent" as considered in the context of this embodiment of the invention should be taken to include:
  i) all suitable therapeutic active agents;
  ii) all suitable anaesthetic active agents;
  iii) all suitable diagnostic active agents; and
  iv) all suitable cosmetic active agents.

It will be appreciated that members of the TGF-β superfamily constitute preferred active agents that may be incorporated in medicaments and pharmaceutical compositions of the invention. Further specific and illustrative examples of suitable active agents that may be advantageously incorporated in medicaments manufactured in accordance with the invention are considered below.

Since sugars used in the manufacture of medicaments in accordance with the invention are generally inert substances they can be combined in medicaments with many suitable active agents without adverse reaction. Sugars used in medicaments manufactured in accordance with the invention do not tend to compromise the activity of other active agents that may be incorporated in the medicaments, nor do they tend to reduce the shelf life of compositions comprising such active agents.

Medicaments manufactured in accordance with the invention provide many advantages over the local anaesthetics that are commonly used in many existing strategies for the prevention or reduction of injection pain. One major advantage conferred by medicaments manufactured in accordance with the invention is that the medicaments (being based around the use of sugars) carry a much lower risk of adverse reactions than do existing anaesthetic preparations. World Health Organisation guidelines suggest that in a number of contexts where local anaesthetics are employed it is recommended that medical staff present are trained in the use of anaesthetics, and also that emergency equipment, including oxygen and resuscitation equipment, be provided on site. As will be appreciated, to meet these requirements involves considerable cost, both in terms of training and necessary equipment.

In contrast, medicaments prepared in accordance with the present invention are both safe and easy to use. Persons administering medicaments manufactured in accordance with the invention do not require specific anaesthetic training, merely the ability to perform injections. The skills needed to give injections can be readily taught to patients, and since there is no need for provision of emergency equipment patients are able to self-administer the medicaments, and thus obtain the benefits of injection pain reduction, within their own homes.

The sugars used in medicaments manufactured in accordance with the invention are not generally associated with dangerous sensitivity reactions that may be occur with anaesthetics commonly used in existing anti-injection pain strategies. By way of example, hypersensitivity to lignocaine (a commonly used local anaesthetic) is generally recognised as a major adverse side effect of the use of this local anaesthetic.

Intravascular injections of even small amounts of local anaesthetic can produce potentially toxic blood levels. Accordingly it is a recognised aim of research to produce medicaments able to reduce injection pain without the need for administration of local anaesthetics. Medicaments of this type may be of particular use in tissues, such as the mouth, that contain many blood vessels, and hence are associated with a heightened risk of accidental intravascular injection.

In contrast, the effect of medicaments manufactured in accordance with the present invention is provided by sugars which are readily metabolised, and which are generally associated with a very low risk of adverse reactions. Accordingly it is a preferred embodiment of the invention that the medicaments be used in the prevention or reduction of injection pain in patients predisposed to heightened sensitivity to local anaesthetics, and particularly preferably in those predisposed to lignocaine hypersensitivity.

A further advantage of medicaments manufactured in accordance with the present invention, when compared with the use of local anaesthetics described in the prior art, is that the medicaments of the invention do not cause blood vessel constriction, which commonly occurs as a result of the administration of known local anaesthetics. Such constriction of blood vessels (which may particularly be caused by pre-administration of local anaesthetics) can render the administration of intra-blood vessel injections difficult. This disadvantage is obviated by medicaments manufactured in accordance with the present invention. Indeed, the use of medicaments manufactured in accordance with the present invention in the prevention or reduction of injection pain associated with intra-blood vessel injections constitutes a preferred embodiment of the invention.

Medicaments manufactured in accordance with the invention also constitute a remarkably cost-effective way of reducing injection pain. In contrast with expensive local anaesthetics, cooling agents, and the like used in existing strategies designed to reduce injection pain, the medicaments manufactured in accordance with the invention utilise relatively inexpensive sugars. Accordingly medicaments manufactured in accordance with the invention offer a notable advantage over the prior art by virtue of their low cost of manufacture.

Medicaments manufactured in accordance with the invention may be of particular advantage to individuals requiring repetitious administration of injections. For example, the medicaments of the invention may be particularly suitable for use by diabetics. When used by individuals suffering from diabetes medicaments manufactured in accordance with the seventh aspect of the invention may be used to reduce the injection pain associated with injections required for the control or regulation of diabetes, such as injections of insulin or glucagon. It will be appreciated that medicaments of the invention incorporating TGF-β superfamily members, such as TGF-$β_3$, may be particularly preferred for use by patients requiring repeated injections to sites of wound healing. In particular these may be useful for patients suffering from conditions of aberrant wound healing, such as suffering from chronic wounds or from pathological scars.

As mentioned above, the inventors have found that the beneficial effects conferred by pharmaceutical compositions in accordance with the invention can be obtained using any sugar thus far tested. Indeed, the inventors have found that sugar salts or derivatives may be used effectively in the manufacture of medicaments in accordance with the invention. However, it may be preferred that pharmaceutical compositions in accordance with the invention comprise a sugar selected from the group comprising maltose, sucrose, glucose and mannose. More preferably the sugar utilised in pharmaceutical compositions in accordance with the invention may be selected from the group comprising maltose and sucrose, and most preferably the sugar is maltose. The use of maltose provides particular advantages in that it demonstrates the greatest efficacy in not only preventing injection pain, but also lessening the effects of erythema that may otherwise be associated with injections.

Except for where the context requires otherwise, references to sugars in the context of medicaments for the reduction of injection pain should also be taken to encompass pharmaceutically acceptable salts, derivatives and variants of sugars. Such salts, derivatives and variants may preferably be salts, derivatives or variants of sugars selected from the group comprising maltose, mannose, sucrose and glucose, most preferably maltose.

It may be preferred that a medicament manufactured in accordance with the invention may comprise a sugar provided at a concentration of greater than 50 mg/ml. Such medicaments may comprise a sugar at a concentration of between 51 and 200 mg/ml, preferably at a concentration of between 60 and 150 mg/ml, more preferably at a concentration of between 70 and 100 mg/ml, even more preferably at a concentration of between 80 and 95 mg/ml, and most preferably at a concentration of between 85 and 90 mg/ml.

Alternatively or additionally, a medicament manufactured in accordance with the invention may comprise a sugar provided at a concentration of between 0.001 and 5M, or of between 0.005 and 2 M. Preferably the sugar is provided at a concentration of between 0.01 and 1 M, more preferably at a concentration of between 0.1 and 0.5, even more preferably at a concentration of between 0.2 and 0.4, and most preferably at a concentration of about 0.25 M.

Medicaments manufactured in accordance with the present invention are particularly suited to administration to the skin, for example by intradermal or subcutaneous injection. However, the medicaments may also be used effectively in the prevention or reduction of injection pain associated with injections at other body sites, for example injections administered to the eye; injections administered to the mouth and digestive system; injections administered to the nervous system; injections in the urino-genital system; or injections in the respiratory system; kidneys; tendons; ligaments; heart or circulatory system.

The medicaments of the invention are particularly suitable for use in injections at sites where existing inflammation may otherwise increase the degree of injection pain that is perceived by a patient receiving an injection. Accordingly the medicaments of the invention may preferably be used for the prevention or reduction of injection pain on injection into an inflamed site. Such inflamed sites may include sites of wounds or abrasions, arthritic sites (including injection sites subject to osteoarthritis, rheumatoid arthritis, and spondyloarthropathies); inflamed sites associated with multiple sclerosis; sites subject to an allergic reaction (including allergic rhinitis/sinusitis; skin allergies including urticaria/hives; angioedema; ectopic dermatitis; inflammation associated with food allergies; inflammation associated with drug allergies or insect allergies; or inflammation associated with other specific allergic disorders such as mastocytosis), autoimmune conditions (including systemic lupus erythematosus; dematomyositis and polymyositis); inflammatory neuropathies such as Guillain Bané and inflammatory polyneuropathies; vasculitis such as Wegener's granulomatosus or polyarteritis nodosa; and other autoimmune conditions such as polymyalgia rheumatica; temperal arteritis, Sjogren's syndrome; Bechet's disease; Churg-Strauss syndrome and Takayasu's arteritis.

The medicaments of the invention may also be of benefit in cases of injection at sites of cardiovascular inflammation, gastrointestinal inflammation, infection or other sites involving an immune reaction, neuroinflammatory disorders and transplant sites.

It is a recognised risk of the use of conventional local anaesthetics that, when used on broken skin such as that found in inflamed, wounded or infected areas, there is a tendency for increased anaesthetic uptake through the broken skin to lead to the development of a systemic, rather than local, reaction. This is particularly notable in the case of topically applied local anaesthetics.

In contrast, medicaments manufactured in accordance with the invention confer a marked advantage in terms of their improved safety since, even in the event of systemic uptake, the sugars used in their preparation are not associated with any ill effects. Accordingly it is a preferred embodiment of the invention that the medicaments be used in the prevention or reduction of injection pain associated with injections at sites of broken skin. It is particularly preferred, as noted elsewhere, that medicaments manufactured in accordance with the invention be used in the prevention or reduction of injection pain associated with injections at sites of inflammation; wound sites (including transplant sites); or infected areas.

Medicaments manufactured in accordance with the invention may incorporate active agents that are beneficial in the treatment and/or management of wounded areas. Examples of active agents that may be advantageously incorporated in medicaments to be administered by injection at wound sites include:

i) Therapeutic active agents, particularly those having a beneficial effect on wound healing or scar formation. Suitable therapeutic active agents may be able to promote or accelerate the wound healing response and/or able to prevent or inhibit scar formation. Examples of such suitable therapeutic active agents include TGF-β superfamily members (as discussed in more detail below) and agents able to neutralise the function of fibrogenic growth factors.

ii) Anaesthetic active agents. There are a number of contexts in which it may be advantageous to administer anaesthetic active agents to wounded areas, for example to facilitate cleaning, closure or dressing of the wound.

Therapeutic active agents having a beneficial effect on wound healing suitable for incorporation in medicaments manufactured in accordance with the present invention should be taken to encompass any substance having a beneficial effect on wound healing. Substances having a beneficial effect on wound healing may, for example, include substances capable of initiating or stimulating the naturally occurring wound healing response, as well as those substances capable of accelerating the wound healing response.

In a ninth aspect of the invention there is provided a method of preventing or reducing injection pain associated with administration of an injection at a wound site, the method comprising administering, by injection at a wound site, a therapeutically effective amount of a medicament comprising a sugar to a patient in need of such injection pain prevention or reduction. A therapeutically effective amount in the context of this aspect of the invention will be an amount of a medicament sufficient to prevent or reduce the injection pain perceived by the patient to whom the medicament is administered. Medicaments to be administered in accordance with this aspect of the invention may preferably further comprise an active agent suitable for the promotion of wound healing and/or the prevention of scar formation. Preferred examples of such active agents may include TGF-β superfamily members, and more preferably may include TGF-β3.

It will be appreciated by those of skill in the art that medicaments manufactured in accordance with the present invention and comprising an active agent of benefit to the wound healing process may also be administered to a patient prior to wounding. Suitable active agents may include those capable of promoting healing and/or of preventing or inhibiting scar formation, such as TGF-β superfamily members. Alternatively, or additionally, medicaments manufactured in accordance with the present invention may contain an anaesthetic useful in preventing pain that may otherwise be caused by a wound to be formed.

It is well recognised that one of the more common medical procedures giving rise to injection pain is the administration by injection of anaesthetic agents. Although such agents may be able to effectively reduce pain once they have been administered and sufficient time has elapsed to allow them to achieve their anaesthetic activity, the injection by which they are administered is frequently a cause of considerable pain to the recipient.

Although it is an aim of certain embodiments of the invention to provide a means by which to avoid or reduce the use of known anaesthetics, particularly in contexts in which their use may give rise to unwanted and/or dangerous side effects, it will be appreciated by the skilled person that medicaments manufactured in accordance with the present invention may be used as suitable "carriers" for anaesthetic active agents (such as injectable anaesthetics). When used in this way medicaments manufactured in accordance with the invention serve to prevent or reduce injection pain that would otherwise be associated with administration of the anaesthetic active agent. Thus in an alternative preferred embodiment a medicament manufactured in accordance with the invention may further comprise an anaesthetic active agent. For the purposes of the present invention an anaesthetic active agent suitable for incorporation in medicaments manufactured in accordance with the present invention may be taken to be any substance having anaesthetic properties. A suitable anaesthetic active agent for incorporation in medicaments manufactured in accordance with the invention may be an injectable local anaesthetic. In a particularly preferred embodiment of the invention the anaesthetic active agent is the local anaesthetic lignocaine.

Medicaments manufactured in accordance with this embodiment of the invention are suitable for use in all contexts in which anaesthetics may be administered by injection. Examples of such contexts will be well known to the skilled person and are considered elsewhere in the specification.

However, there are a number of contexts in which medicaments manufactured in accordance with the invention particularly beneficially used to prevent or reduce injection pain associated with the injection of local anaesthetics.

Thus in one preferred example, medicaments manufactured in accordance with the present invention may be used to prevent or reduce injection pain associated with the injection of local anaesthetics in the mouth. Injection pain associated with injection of local anaesthetics in the mouth has been shown to be particularly traumatic for patients and it is believed that this increase in trauma arises as a result of the fact that the pain is perceived as associated with the head of the patient. This location both increases the degree of injection pain perceived by the patient and also amplifies the unpleasantness of such pain. Furthermore, the increased perception of pain by the patient also exacerbates the trauma experienced by a medical or dental practitioner administering such injections.

Medicaments manufactured in accordance with the invention may also be used for the prevention or reduction of injection pain associated with injections of anaesthetic at other sites on or in the heads of patients, particularly with injection of anaesthetic at sites on the face of patients.

As described previously, the medicaments of the invention may also be used as "carriers" for diagnostic active agents, thereby reducing or preventing injection pain that might otherwise be associated with the administration of the diagnostic active agent. Examples of diagnostic active agents that may be administered by injection, and that may therefore advantageously be incorporated in medicaments manufactured in accordance with the invention include radiopaque agents. Such diagnostic active agents are administered to a patient by way of injection (for example into blood vessels or the cerebrospinal fluid) and their ability to absorb x-rays used as an aid to diagnosis. Examples of suitable diagnostic active agents that may be incorporated in medicaments manufactured in accordance with the invention include diatrizoates, iohexyl, iopamidol, iothalamate, ioversol, ioxaglate, and metrizamide. These radiopaque diagnostic active agents may be used in the diagnosis of diseases or conditions such as biliary tract problems, blood vessel diseases, blood vessel diseases of the brain, blood vessel diseases of the heart, brain diseases and tumours, breast lesions, heart disease, impaired flow of cerebrospinal fluid in the brain, kidney diseases, joint diseases, liver diseases, pancreas diseases, spinal diseases such as spinal disc diseases, spleen diseases, stomach and intestinal problems, or urinary tract problems.

Medicaments manufactured in accordance with the invention may advantageously incorporate cosmetic active agents. There are many cosmetic active agents that are typically administered to patients by means of injection. For example, botulinum toxin injections (more commonly known as "botox" injections) are usually administered by intradermal injection of the toxin at a requisite site of a patient. Botulinum toxin injections are frequently administered to sites on the face or neck of patients being treated, and this administration is normally associated with injection pain that may be alleviated by the incorporation of botulinum toxin in medicaments manufactured in accordance with the invention.

Another cosmetic procedure involving administration of cosmetic active agents by injection, and hence associated injection pain, is the injection of cosmetic fillers. These active agents (which typically include collagen, hyaluronic acid, fat and other related substances) may be administered by injection at sites where it is desired to "fill out" the skin, for example filling wrinkles associated with aging, augmenting the profile of the lips, or filling scars such as those caused by acne. Injection pain associated with the administration of cosmetic fillers may be prevented or reduced by the incorporation of suitable cosmetic fillers in medicaments manufactured in accordance with the invention.

The inventors have found that the prevention or reduction of injection pain is provided by medicaments manufactured in accordance with the invention in respect of all routes of injection investigated.

By way of example, the inventors have found that medicaments in accordance with the invention may be used for the prevention or reduction of injection pain associated with intradermal injection. Accordingly, in a preferred embodiment of the invention a suitable medicament may be an intradermally injectable medicament for the prevention or reduction of injection pain associated with intradermal injection.

The inventors have also found that medicaments in accordance with the invention may be used for the prevention or reduction of injection pain associated with subcutaneous injection. Accordingly, in another preferred embodiment of the invention a suitable medicament may be a subcutaneously injectable medicament for the prevention or reduction of injection pain associated with subcutaneous injection.

The inventors have further found that medicaments in accordance with the invention may be used for the prevention or reduction of injection pain associated with intravenous injection. As previously noted, medicaments manufactured in accordance with the invention may be advantageously used in intra-blood vessel injections since they are able to prevent or reduce injection pain without contributing to blood vessel constriction. Accordingly, in a further preferred embodiment of the invention, a suitable medicament may be an intravenously injectable medicament for the prevention or reduction of injection pain associated with intravenous injection.

The inventors have still further found that medicaments in accordance with the invention may be used for the prevention or reduction of injection pain associated with intramuscular injection. Accordingly, in a still further preferred embodiment of the invention a suitable medicament may be an intramuscularly injectable medicament for the prevention or reduction of injection pain associated with intramuscular injection.

The inventors have still further found that medicaments in accordance with the invention may be used for the prevention or reduction of injection pain associated with intraperitoneal injection. Accordingly, in a still further preferred embodiment of the invention a suitable medicament may be an intramuscularly injectable medicament for the prevention or reduction of injection pain associated with intraperitoneal injection.

It is particularly preferred that medicaments manufactured in accordance with the invention may be formulated for intradermal injection, or may be formulated for subcutaneous injection. Typical formulations suitable for intradermal injection and/or subcutaneous injection will be well known to those skilled in the art.

Although the pharmaceutical compositions and methods of treatment of the present invention are particularly suitable for use in humans, and have largely been described with reference to such use, it will be appreciated that they are also susceptible to use in non-human animals; and particularly in domestic or agricultural animals such as dogs, cats, cattle and horses.

EXPERIMENTAL RESULTS

TGF-$\beta_3$ Bulk Material

The TGF-$\beta$ superfamily member TGF-$\beta_3$ was supplied in a stock solution at a concentration of 9.1 mg/mL in 20 mM acetic acid and 20% (v/v) isopropyl alcohol. This stock solution was serially diluted to produce compositions incorporating the TGF-$\beta$ superfamily member TGF-$\beta_3$. The concentrations of TGF-$\beta_3$ incorporated in the compositions used in the following experiments were as described below.

A. Recovery of TGF-$\beta_3$ from Pre-Filled Syringes Containing Pharmaceutical Compositions.

The following experiment investigated the recovery of the TGF-$\beta$ superfamily member TGF-$\beta_3$ from pre-filled syringes containing compositions either in accordance with the invention, or in accordance with the prior art.

A1. Production of Pre-Filled Syringes.

Compositions incorporating the TGF-$\beta$ superfamily member TGF-$\beta_3$ at a concentration of 1 μg/100 μL were produced by serial aseptic dilution from the bulk material described above. The diluents used to produce the test compositions in accordance with the present invention were as follows:

i) 0.25 M maltose (equivalent to 90 mg/ml);
ii) 0.25 M glucose (equivalent to 45 mg/ml);
iii) 0.25 M sucrose (equivalent to 86 mg/ml); and
iv) 0.25 M mannose (equivalent to 45 mg/ml).

For comparison purposes, a composition representing preferred prior art compositions was produced by dilution of the stock solution to produce a 1 μg/100 μL solution of TGF-$\beta_3$ in DS11 (a diluent comprising phosphate buffered saline PBS and 5% (w/v) mannitol).

750 μL samples of each of the compositions formed were drawn up into individual sterile 1 mL syringes. Thus each syringe contained a defined amount of an experimental or comparison composition in which was incorporated a known quantity of the TGF-$\beta$ superfamily member TGF-$\beta_3$. The syringes containing the compositions of the invention and those containing the prior art composition were then stored at 4° C. for one week. These experimental storage conditions provided a model of the typical manner in which pharmaceutical compositions are stored refrigerated prior to their therapeutic use.

In order to evaluate the quantity of TGF-$\beta_3$ recoverable from the compositions of the invention and prior art composition, the contents of the syringes were recovered (through expulsion from the syringe) and the amount of recoverable TGF-$\beta_3$ protein evaluated by ELISA as described below.

A2. Assessment of TGF-$\beta$ Recovery by ELISA

The following assay was used to compare recovery of the TGF-$\beta$ superfamily member TGF-$\beta$ from pharmaceutical compositions in accordance with the invention with the amount of TGF-$\beta_3$ recoverable from prior art compositions. The assay may be readily adapted, by substitution of suitable capture and detection antibodies and use of a suitable standard curve, to allow assessment of recovery of other TGF-$\beta$ superfamily members from pharmaceutical compositions of interest (for example other compositions in accordance with the invention, or other control compositions known from the prior art).

A2.1. Preparation of Plates for ELISA.

Ninety-six well plates (Falcon 353912) were coated with 100 μL/well of a monoclonal anti-TGF-$\beta_3$ capture antibody (R&D Systems MAB643) diluted in PBS to a concentration of 2 μg/mL. The plates were then sealed and incubated overnight at room temperature to allow the antibody to adhere to the wells. After incubation each well was aspirated and washed three times with 300 μL/well (each wash) of wash buffer (comprising 0.05% (v/v) Tween 20 in PBS, pH 7.4). Non-specific protein binding sites were blocked by the addition of 150 μL/well of PBS containing 1% (w/v) BSA, 5%

(w/v) sucrose and 0.05% (w/v) sodium azide. Wells containing this solution were incubated at room temperature for one hour.

A2.2. Preparation of TGF-$\beta_3$ Standard Curve

All standard and sample dilutions were made in either 0.25 M sugar solution (i.e. maltose, glucose, mannose or sucrose) or ELISA diluent (0.1% (w/v) BSA, 0.05% (v/v) Tween 20 in Tris-buffered saline pH 7.3).

A TGF-$\beta_3$ standard series using human recombinant TGF-$\beta_3$ (R&D Systems 243-B3) or TGF-$\beta_3$ (from the stock solution at a concentration of 9.1 mg/mL in 20 mM acetic acid and 20% (v/v) isopropyl alcohol), ranging from 31.25 pg/mL to 2000 pg/mL, was prepared.

A2.3. Recovery Assay

A volume of 100 µL of either the sample or standard solutions was added to each well. The plate was then sealed and incubated for 1.5 hours at room temperature. The wells were then aspirated and washed a total of three times with 300 µL/well of wash buffer (as above) for each wash.

Once the wells had been aspirated and washed, a volume of 100 µL of biotinylated anti-TGF-$\beta_3$ detection antibody (R&D Systems BAF243) diluted to 100 ng/mL in ELISA diluent (as before) was added to each well. The plate was then sealed and incubated for 1.5 hours at room temperature. The wells were then aspirated and washed a total of three times with 300 µL/well of wash buffer (as before) for each wash. A volume of 100 µL/well of Streptavadin HRP (Dako P0397) diluted 1:5000 in ELISA diluent was then added to each well, and the plate sealed and incubated for 30 minutes at room temperature. The wells were then aspirated and washed a total of three times, using 300 µL/well of wash buffer for each wash. A volume of 100 µL of Substrate Solution (R&D Systems DY999) was then added to each well, the plate covered and incubated for 20 minutes at room temperature. A volume of 50 µL of Stop Solution (0.5 M $H_2SO_4$) was then added to each well. The optical density of the contents of each well was then determined, within 30 minutes, using a microplate reader at a wavelength of 450 nm (wavelength correction set to 570 nm). The quantity of TGF-$\beta_3$ present in the samples, representing TGF-$\beta_3$ recoverable from the compositions, was then determined by reference to the standard curve. The results are expressed in Table 1 below, as the fold increase of material recovered from the syringe compared to the DS11 (mannitol) formulation representative of preferred compositions known in the prior art.

A3. Results of Recovery Assay

The recoverable TGF-$\beta_3$ detected in a PBS/Mannitol (DS11) formulation was 284.8 (±0.03) ng/100 µL.

The fold-increase in recovery of TGF-$\beta_3$ from syringes containing compositions in accordance with the invention following one week storage at 4° C. (compared to TGF-$\beta_3$ recovery from syringes containing the DS11 formulation subjected to the same storage conditions) is shown below in Table 1.

The results clearly indicate that pharmaceutical compositions in accordance with the present invention allow greatly increased recovery of the TGF-$\beta$ superfamily member incorporated therein as compared to the level of recovery possible using preferred compositions known from the prior art.

TABLE 1

| Formulation | Fold Increase in Recoverable Material Compared to DS11 Formulation |
| --- | --- |
| Sucrose | 3.18 |
| Maltose | 4.91 |
| Glucose | 2.18 |
| Mannose | 2 |

B. Biological Activity of TGF-$\beta$ Superfamily Members Incorporated in Pharmaceutical Compositions in Accordance with the First Aspect of the Invention.

The inherent biological activity of the TGF-$\beta$ superfamily member TGF-$\beta_3$ incorporated in compositions of the invention was determined in accordance with the following assay, which utilises the ability of TGF-$\beta$ superfamily members to inhibit mink lung epithelial cell proliferation. The biological activity of the incorporated TGF-$\beta$ superfamily member may then be assessed by determining its $IC_{50}$ value (the concentration at which 50% inhibition of the cells' proliferation response is observed).

This assay represents a suitable means by which the biological activity of other TGF-$\beta$ superfamily members incorporated in compositions of the invention, or in known compositions used for comparison purposes, may be determined.

B1. Experimental details of Biological Activity Assay.

Briefly, the biological activity of TGF-$\beta_3$ incorporated in a composition in accordance with the first aspect of the invention was determined by measurement of the inhibition of proliferation of Mink lung epithelial cells (Mv-1-Lu) (ATCC Cat no CCL-64) brought about by the TGF-$\beta$ superfamily member. Inhibition of proliferation was assessed using a MIT reagent (Sigma Cat No M2279). MTT is 3-(4,5-Dimethyl-2-thiazolyl)-2,5-diphenyl-2H-tetrazolium bromide, a soluble tetrazolium salt that is converted to its insoluble formazan product by the metabolic activity (mitochondrial dehydrogenases) of cells. The insoluble formazan crystals are solubilized with acidified isopropanol and the intensity of the resultant solution is measured colorimetrically at a wavelength of 570 nm.

Briefly, $1\times10^4$/ml of Mink lung epithelial cells were inoculated into 96-well plates in 100 µl of culture medium (DMEM+10% (v/v) Foetal Bovine Serum, 20 mM Glutamine, 0.1M Hepes) per well. The cells were incubated at 37° C. in 5% (v/v) $CO_2$, and allowed to attach for 24 hours. TGF-$\beta_3$ was diluted just prior to use (i.e. without storage) in DS11, comprising phosphate buffered saline (PBS) containing 5% (w/v) mannitol, or 0.25 M maltose to generate standard curves at ten times the final assay concentration of 1.9-500 pg/mL. The samples were then further diluted 1:5 in cell culture medium prior to the addition of 100 µL of these samples to each well containing 100 µL of cell culture medium (resulting in a further 1:2 dilution in the well and therefore final assay concentrations of 1.9-500 pg/mL). The cells of each well were then exposed to samples for five days at 37° C. in 5% (v/v) $CO_2$. At the end of the exposure, 50 µl of MIT reagent (2 mg/mL stock diluted in PBS) was then added to each well. The plates were then incubated for a further four hours at 37$\beta$ C. in 5% (v/v) $CO_2$. After this period the supernatant from each well was removed and the precipitated formazan crystals were dissolved by the addition of 100 µl/well of acid isopropanol. The solubilised MIT in each well was then quantified using a 96-well plate reader at a wavelength of 570 nm. The data were plotted using XLFit 3 and the $IC_{50}$ values calculated for five individual curves for each formulation. The $IC_{50}$ value for each formulation was then expressed as the mean (±standard deviation) of these individual standard curves.

B2. Results of Biological Activity Assay.

Figure 2:
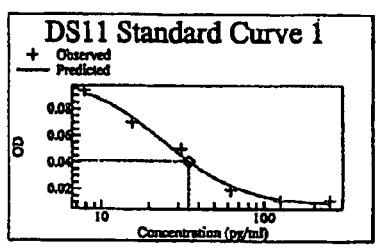
FIG. 2 illustrates, in panels 2A to 2J, the results of experiments to compare the inherent biological activity of the TGF-β superfamily member TGF-β3 when incorporated in pharmaceutical compositions according to the invention, or in pharmaceutical compositions of the prior art.
Figure 2:
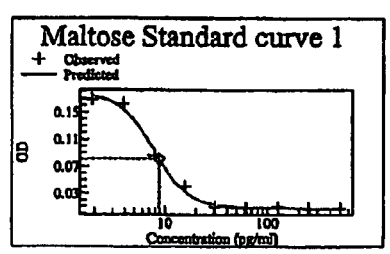
Figure 2:
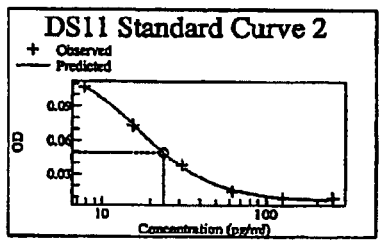
Figure 2:
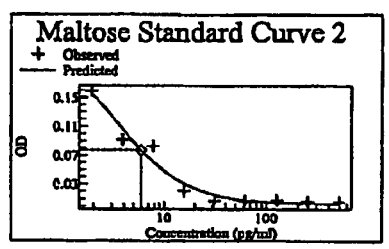
Figure 2:
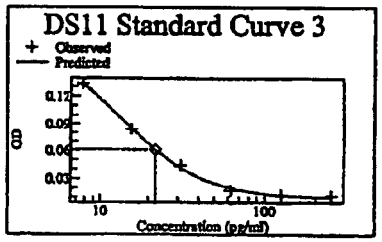
Figure 2:
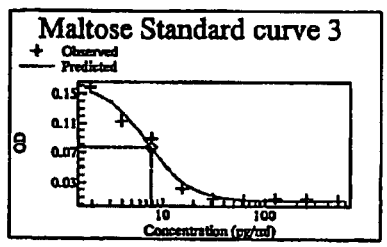
Figure 2:
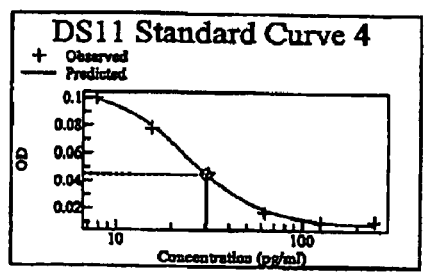
Figure 2:
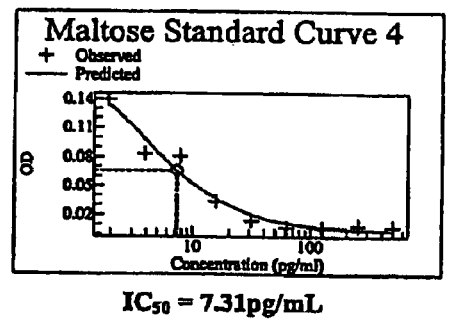
Figure 2:
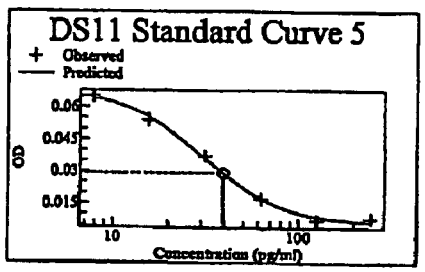
Figure 2:
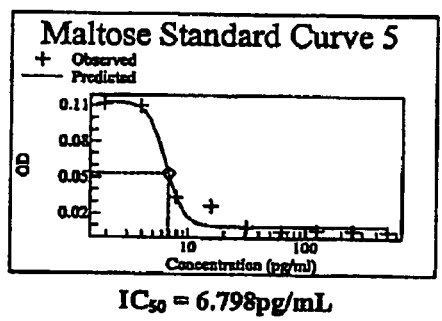

The results of five repetitions of the biological activity assay using both a known composition of the prior art (FIGS. 2A to 2E) and a composition of the invention (FIGS. 2F to 2J) are shown in FIG. 2. The means (±the standard deviation) of the individual curves shown in FIG. 2 are provided in Table 2.

The results clearly illustrate that the 1050 value (for the inhibition of mink lung epithelial cell proliferation) of TGF-$\beta_3$ incorporated in pharmaceutical compositions in accordance with the invention is greatly reduced in as compared to the value obtained for TGF-$\beta_3$ incorporated in preferred prior art compositions. This decrease in the IC50 value indicates that the amount of the TGF-$\beta$ superfamily member TGF-$\beta_3$ required to achieve 50% of the biological activity exerted by the cytokine is reduced when incorporated in the pharmaceutical compositions of the invention. Accordingly, the biological activity of the TGF-$\beta$ superfamily member incorporated in compositions of the invention can be seen to be much increased over that which can be achieved using compositions of the prior art.

TABLE 2

| Formulation | Mean $IC_{50}$ (pg/mL; ±standard deviation) |
|---|---|
| DS11 | 30.104 (±7.093) |
| Maltose | 7.309 (±1.044) |

D. Summary of Studies A and B

Pharmaceutical compositions in accordance with the present invention allow surprisingly high levels of recovery of TGF-$\beta$ superfamily members incorporated in the compositions as compared to the preferred compositions described in the prior art. Furthermore, the biological activity of the TGF-$\beta$ superfamily members incorporated in the compositions is surprisingly increased as compared to TGF-$\beta$ superfamily members incorporated in prior art compositions.

E. Evaluation of Localised Pain and Erythema Associated with Intradermal Injection of Formulations A study was conducted to evaluate localised pain and erythema associated with intradermal injection of medicaments manufactured in accordance with the invention and the pain and erythema associated with control injections of prior art compositions.

Experimental injectable solutions were prepared as described above.

Briefly, a volume of 100 µL of each formulation described above was injected intradermally into the inner aspect of the upper arms of a volunteer. In addition to the DS11 control described above, a solution of the known local anaesthetic lignocaine was also used as a further control. The pain on injection and erythema were categorised by the volunteer and a clinician.

Separate evaluations of local pain and erythema associated with each of the solutions shown in Table 3 were undertaken. Both the volunteer and the clinician undertook these evaluations. The extent of pain or erythema associated with the different formulations used was rated based upon the following categories (listed in ascending severity):

i) none
ii) minimal
iii) slight
iv) marked

The results of the evaluation are shown in Table 3 and these are further summarised in Table 4.

The results indicate that medicaments manufactured in accordance with the invention consistently gave rise to reduced injection pain when compared to injectable compositions known from the prior art.

The results clearly illustrate the suitability of medicaments manufactured in accordance with the invention for use as carriers able to reduce the injection pain that would otherwise be associated with injection of other substances. This is particularly illustrated by the finding that medicaments in accordance with the invention that incorporated mannitol gave rise to less injection pain than did injections of mannitol-base compositions alone.

F. Summary of Study E

Medicaments manufactured in accordance with the present invention possess a surprising ability to prevent or reduce injection pain. This ability is exhibited both in comparison to known anaesthetic agents (such as lignocaine) and in comparison to existing preferred injectable medicaments (such as the mannitol-based formualation DS11). The beneficial properties of medicaments manufactured in accordance with the invention are exhibited by all sugars tested thus far, but are not exhibited by a formulation consisting of the sugar alcohol mannitol.

TABLE 3

| Sample | Volunteer | Erythema | Pain |
|---|---|---|---|
| Lignocaine | 1 | Marked | Marked |
| Water containing 5% mannitol and equiv 100 µg/100 µL protein | | Slight | Slight |
| Glucose | | Slight | None |
| Mannose | | Minimal | None |
| Maltose | | Minimal | None |
| Sucrose | | Minimal/None | None |
| Mannose + 5% mannitol | | Minimal | Minimal |
| Glucose + 5% mannitol | | Minimal | Minimal |
| Sucrose + 5% mannitol | | Minimal | Minimal |
| Maltose + 5% mannitol | | None | Minimal |
| Lignocaine | 2 | Marked | Marked |
| Maltose + 5% mannitol | | None | Minimal |
| Maltose + 5% mannitol | 3 | None | Minimal |

TABLE 4

| Formulation | Erythema | Pain |
|---|---|---|
| Lignocaine (control) | Marked | Marked |
| DS11 | Slight | Slight |
| Sucrose | Minimal | None |
| Maltose | Minimal | None |
| Glucose | Minimal | None |
| Mannose | Minimal | None |

What is claimed is:

1. A pharmaceutical composition comprising a TGF-β and a sugar provided at a concentration effective to (i) improve recovery of the TGF-β3, (ii) increase biological activity of the TGF-β3, or (iii) improve recovery and increase biological activity of the TGF-β3, compared to a mannitol-based composition comprising the TGF-β3, wherein the biological activity comprises promotion of wound healing or inhibition or reduction of scar formation, wherein the sugar is selected from maltose, sucrose, glucose and mannose, and the sugar is present at a concentration of greater than 50 mg/ml.

2. The pharmaceutical composition of claim 1, wherein the sugar is maltose.

3. The pharmaceutical composition of claim 1, wherein the sugar is selected from the group consisting of glucose and mannose.

4. The pharmaceutical composition of claim 1, wherein the sugar is present at a concentration of between 51 and 200 mg/ml.

5. The pharmaceutical composition of claim 1, wherein the sugar is present at a concentration of between 60 and 150 mg/ml.

6. The pharmaceutical composition of claim 1, wherein the sugar is present at a concentration of between 70 and 100 mg/ml.

7. The pharmaceutical composition of claim 1, wherein the sugar is present at a concentration of between 80 and 95 mg/ml.

8. The pharmaceutical composition of claim 1, wherein the sugar is present at a concentration of between 85 and 90 mg/ml.

9. A soluble pharmaceutical composition comprising a TGF-β3 and a sugar, wherein the sugar is provided in such a proportion that, on dissolution of the composition to achieve a physiological solution, the sugar is at a concentration effective to (i) improve recovery of the TGF-β3, (ii) increase biological activity of the TGF-β3, or (iii) improve recovery and increase biological activity of the TGF-β3, compared to a mannitol-based composition comprising the TGF-β3, wherein the biological activity comprises promotion of wound healing or inhibition or reduction of scar formation, wherein the sugar is selected from maltose, sucrose, glucose and mannose, and the sugar is present at a concentration of greater than 50 mg/ml.

10. A soluble pharmaceutical composition comprising a TGF-β3, a source of sodium ions, and a sugar, the quantities of the source of sodium ions and of the sugar being such that on dissolution of the composition to produce a sodium concentration of between 130 and 160 mEq/L, and the concentration of the sugar is effective to (i) improve recovery of the TGF-β3, (ii) increase biological activity of the TGF-β, or (iii) improve recovery and increase biological activity of the TGF-β3, compared to a mannitol-based composition comprising the TGF-β3, wherein the biological activity comprises promotion of wound healing or inhibition or reduction of scar formation, wherein the sugar is selected from maltose, sucrose, glucose and mannose, and the sugar is present at a concentration of greater than 50 mg/ml.

11. The pharmaceutical composition of claim 1, wherein the biological activity is the promotion of wound healing.

12. The pharmaceutical composition of claim 1, wherein the biological activity is the inhibition of scar formation.

13. The pharmaceutical composition of claim 1, wherein the composition is formulated for administration by injection.

14. The pharmaceutical composition of claim 13, wherein the composition is formulated for administration by intradermal injection.

15. The pharmaceutical composition of claim 13, wherein the composition is formulated for administration by subcutaneous injection.

16. The pharmaceutical composition of claim 13, wherein the composition is formulated for administration by intravenous injection.

17. The pharmaceutical composition of claim 13, wherein the composition is formulated for administration by intramuscular injection.

18. The pharmaceutical composition of claim 1, wherein the composition is formulated for administration as an intraperitoneal instillate.

19. The pharmaceutical composition of claim 1, wherein the composition is formulated for administration as an eye drop.

20. The pharmaceutical composition of claim 1, wherein the composition is formulated for administration via a stent.

21. The pharmaceutical composition of claim 1, wherein the composition is formulated for administration by a slow release vehicle.

22. The pharmaceutical composition of claim 1, wherein the composition comprises a thickening agent.

23. The pharmaceutical composition of claim 1, wherein the composition comprises a thixotropic agent.

24. A pre-filled container comprising a pharmaceutical composition in accordance with claim 1.

25. The pre-filled container of claim 24, wherein the container is a syringe.

26. The pre-filled container of claim 24, wherein the container is a vial.

27. A method of promoting wound healing and/or inhibiting scar formation in a patient in need thereof, the method comprising administering to a patient in need of such promotion and/or inhibition a therapeutically effective amount of a pharmaceutical composition according to claim 1.

28. A method for improving the recovery of TGF-β3 and/or increasing the biological activity of TGF-β3 incorporated in a pharmaceutical composition comprising adding a sugar to the composition at a concentration effective to (i) improve recovery of the TGF-β3, (ii) increase biological activity of the TGF-β3, or (iii) improve recovery and increase biological activity of the TGF-β3, compared to a mannitol-based composition comprising the TGF-β3, wherein the biological activity comprises promotion of wound healing or inhibition or reduction of scar formation, wherein the sugar is selected from maltose, sucrose, glucose and mannose, and the sugar is present at a concentration of greater than 50 mg/ml.

29. The method according to claim 28, wherein the sugar is maltose.

30. The pharmaceutical composition of claim 1, wherein the sugar is present at a concentration of between 0.2 and 0.4 M.

31. The pharmaceutical composition of claim 1, wherein the sugar is present at a concentration of about 0.25 M.

* * * * *